US006673931B2

(12) United States Patent
Breu et al.

(10) Patent No.: US 6,673,931 B2
(45) Date of Patent: *Jan. 6, 2004

(54) NAPHTHALENYL PIPERIDINES AS RENIN INHIBITORS

(75) Inventors: Volker Breu, Schliengen (DE); Hans-Peter Märki, Basle (CH); Eric Vieira, Allschwil (CH); Wolfgang Wostl, Grenzach-Wyhlen (DE)

(73) Assignee: Hoffman-La Roche Inc., Nutley, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/023,679

(22) Filed: Dec. 18, 2001

(65) Prior Publication Data

US 2002/0087002 A1 Jul. 4, 2002

Related U.S. Application Data

(62) Division of application No. 09/542,303, filed on Apr. 4, 2000, now Pat. No. 6,376,672.

(30) Foreign Application Priority Data

Apr. 27, 1999 (EP) .............................. 99108199

(51) Int. Cl.[7] ...................... C07D 211/42; A61K 31/445
(52) U.S. Cl. ...................... 546/205; 546/210; 514/316; 514/326
(58) Field of Search ................................ 514/319, 326; 546/205, 210

(56) References Cited

U.S. PATENT DOCUMENTS 6,051,712 A * 4/2000 Binggeli et al. ............ 546/194
6,376,672 B1 * 4/2002 Breu et al. .................. 546/205

FOREIGN PATENT DOCUMENTS

| AU | 81821/91 | 1/1993 |
|---|---|---|
| EP | 0 273 199 | 7/1988 |
| EP | 0339 579 | 11/1989 |
| WO | WO 97/03911 | 3/1997 |
| WO | WO-9912532 A2 * | 3/1999 |

OTHER PUBLICATIONS

Robinson, P.L. et al., Phosphorus and Sulfur, 26, pp 15–24 (1986).
Jaegeer E. and Biel, J.H., J. Org. Chem., 30 (3), pp 740–744 (1965).
Mancuso A.J. and Swern D., Synthesis, p 165–185 (1981).
Houben–Weyl, Organic Chemistry, vol. E21, p 81, (1991).
Fischli W. et al., Hypertension, 18 (1), pp 22–31 (1991).
Clozel J.–P. et al, Hypertension, 22 (1), pp 9–17 (1993).
Pals, D.T. et al., Hypertension, 8, pp 1105–1112 (1986).
Dellaria J.F. et al., J. Med. Chem., 30, pp 2137–2144 (1987).
Kokubu T. et al., Biochem. Biophys. Res. Commun., 118, pp 929–933 (1984).
Boger J. et al., J. Med. Chem., 28, pp 1779–1790 (1985).
Luft F.C. et al., Hypertension, 33, Part II, pp 212–218 (1999).
Mervaala E.M.A. et al, Hypertension, 33, Part II, pp 389–395 (1999).
Vieira E. et al, Bioorganic & Medicinal Chemistry Letters, 9, pp. 1397–1402 (1999).

* cited by examiner

Primary Examiner—Ceila Chang
(74) Attorney, Agent, or Firm—George W. Johnston; Patricia S. Rocha-Tramaloni; Kimberly J. Prior

(57) ABSTRACT

Piperidine derivatives, their manufacture and use as medicaments is described. The compounds are useful for treating diseases associated with restenosis, glaucoma, cardiac infarct, high blood pressure and end organ damage, e.g. cardiac insufficiency and kidney insufficiency.

30 Claims, No Drawings

NAPHTHALENYL PIPERIDINES AS RENIN INHIBITORS

CROSS REFERENCE TO RELATED APPLICATION

This is a divisional of application Ser. No. 09/542,303, filed Apr. 4, 2000, now U.S. Pat. No. 6,376,672.

BACKGROUND OF THE INVENTION

The present invention relates to novel piperidine derivatives, their manufacture and use as medicaments.

SUMMARY OF THE INVENTION

The subject invention provides compounds of the formula:

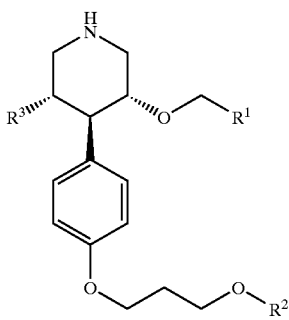

I wherein
- $R^1$ is naphthyl or naphthyl substituted by one to three $C_1$–$C_5$-alkoxy groups;
- $R^2$ is phenyl; phenyl substituted by one to three substituents independently selected from the group consisting of halogen, cyano, $C_1$–$C_3$-alkoxy, and nitro; benzyl; or benzyl substituted by one to three substituents independently selected from the group consisting of halogen, cyano, $C_1$–$C_3$-alkoxy, and nitro;
- $R^3$ is hydroxymethyl, imidazolylmethyl, triazolylmethyl, H—[CH(OR$^4$)]$_2$—CH$_2$—, H—[CH(OR$^4$)]$_2$—CH$_2$—O—CH$_2$—, or $R^{3a}$—(CH$_2$)$_k$—[CH(OR$^4$)]$_1$—CH$_2$—O—;
- $R^{3a}$ is hydrogen, hydroxy, imidazolyl, triazolyl, $C_1$–$C_3$-alkoxy, $C_1$–$C_3$-alkoxy-$C_2$–$C_3$-alkoxy, hydroxy-$C_2$–$C_3$-alkoxy, $C_1$–$C_3$-alkylamino or $C_1$–$C_3$-dialkylamino;
- $R^4$ is hydrogen or $C_1$–$C_3$-alkyl;
- k is 1 or 2, when $R^{3a}$ is hydrogen, k is 0;
- l is 1 or 2; or and pharmaceutically acceptable salts thereof.

While the substituents are above listed collectively, all combinations of the mentioned substituents are enabled and described. For example, $R^1$ can be naphthyl or naphthyl substituted by one to three $C_1$–$C_5$-alkoxy groups, preferably one $C_1$–$C_3$-alkoxy group, such as methoxy, and in particular 4-methoxy-naphthalen-2yl.

Similarly, $R^2$ can be phenyl, or benzyl, or phenyl substituted by one to three substituents independently selected from the group consisting of halogen, cyano, $C_1$–$C_3$-alkoxy, and nitro, or benzyl substituted by one to three substituents independently selected from the group consisting of halogen, cyano, $C_1$–$C_3$-alkoxy, and nitro. Preferred $R^2$s include phenyl substituted by one to three substituents independently selected from the group consisting of halogen, cyano, $C_1$–$C_3$-alkoxy, and nitro, and benzyl substituted by one to three substituents independently selected from the group consisting of halogen, cyano, $C_1$–$C_3$-alkoxy, and nitro. More preferred $R^2$ groups include phenyl substituted by one to three $C_1$–$C_3$-alkoxy groups or by one to three $C_1$–$C_3$-alkoxy groups in combination with one to three halogens. Favorably, $R^2$ is phenyl substituted by one to three $C_1$–$C_3$-alkoxy groups or phenyl substituted by one to three $C_1$–$C_3$-alkoxy groups in combination with one to three halogens. More preferred is where the $C_1$–$C_3$-alkoxy group is methoxy and the halogen is fluorine. Favored situations include $R^2$ being 2-methoxy benzyl, 3-fluoro-2-methoxy-benzyl, 4-fluoro-2-methoxy-benzyl, 5-fluoro-2-methoxy-benzyl, 3,5-difluoro-2-methoxy-benzyl, and 4,5-difluoro-2-methoxy-benzyl.

$R^2$ can also be benzyl substituted by one to three $C_1$–$C_3$-alkoxy groups or by one to three $C_1$–$C_3$-alkoxy groups in combination with one to three halogens. Of these, it is preferred that benzyl be substituted by one to three $C_1$–$C_3$-alkoxy groups or one to three $C_1$–$C_3$-alkoxy groups in combination with one to three halogens, for example 2-methoxybenzyl and fluoro-2-methoxybenzyls, such as. It is especially preferred where $C_1$–$C_3$-alkoxy group is methoxy and the halogen is fluorine.

Preferred $R^3$s include hydroxymethyl, imidazolylmethyl, triazolylmethyl, H—[CH(OR$^4$)]$_2$—CH$_2$—, and H—[CH(OR$^4$)]$_2$—CH$_2$—O—CH$_2$—. Any of these groups can be used. It is preferred, however, when $R^4$ is hydrogen. Also preferred is when $R^3$ is $R^{3a}$—(CH$_2$)$_k$—[CH(OR$^4$)]$_1$—CH$_2$—O—. In such situations it is preferred that $R^{3a}$ is hydroxy or $C_1$–$C_3$-alkoxy, or imidazolyl or triazolyl, $C_1$–$C_3$-alkoxy-$C_2$–$C_3$-alkoxy, or $R^{3a}$ is hydroxy-$C_2$–$C_3$-alkoxy, or $C_1$–$C_3$-alkylamino or $C_1$–$C_3$-dialkylamino. A favored $R^{3a}$ is 2-methoxy-ethoxy. Another is methylamino.

DETAILED DESCRIPTION OF THE PREFERRED EMBODIMENTS

The subject invention will now be described in terms of its preferred embodiments. These embodiments are set forth to aid in understanding the invention but are not to be construed as limiting.

The invention relates to novel piperidine derivatives of general formula I

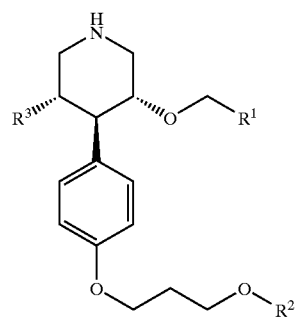

I wherein
- $R^1$ is naphthyl optionally substituted by one to three $C_1$–$C_5$-alkoxy groups;

R² is phenyl or benzyl, optionally substituted by substituents independently selected from one to three halogen, cyano, C₁–C₃-alkoxy and nitro groups;

R³ is hydroxymethyl, imidazolylmethyl, triazolylmethyl, H—[CH(OR⁴)]₂—CH₂—, or H—[CH(OR⁴)]₂—CH₂—O—CH₂—, or R³ᵃ—(CH₂)ₖ—[CH(OR⁴)]₁—CH₂—O—;

R³ᵃ is hydrogen, hydroxy, imidazolyl, triazolyl, C₁–C₃-alkoxy, C₁–C₃-alkoxy-C₂–C₃-alkoxy, hydroxy-C₂–C₃-alkoxy, C₁–C₃-alkylamino or C₁–C₃-dialkylamino;

R⁴ is hydrogen or C₁–C₃-alkyl;

k is 1 or 2, when R³ᵃ is hydrogen, k is 0;

l is 1 or 2; and pharmaceutically acceptable salts thereof.

The present invention also relates to pharmaceutical compositions comprising a compound of formula (I) and a pharmaceutically acceptable carrier and/or adjuvant.

The piperidine derivatives of the present invention have an inhibitory activity on the natural enzyme renin. Accordingly, they can be used for the treatment of disorders which are associated restenosis, glaucoma, cardiac infarct, high blood pressure and end organ damage, e.g. cardiac insufficiency and kidney insufficiency. In addition, the present invention relates to a method for the prophylactic and/or therapeutic treatment of diseases which are associated with restenosis, glaucoma, cardiac infarct, high blood pressure and end organ damage, e.g. cardiac insufficiency and kidney insufficiency, which method comprises administering a compound of formula (I) to a human being or an animal. Furthermore, the present invention relates to the use of such compounds for the preparation of medicaments for the treatment of disorders which are associated restenosis, glaucoma, cardiac infarct, high blood pressure and end organ damage, e.g. cardiac insufficiency and kidney insufficiency.

The present invention also relates to processes for the preparation of the compounds of formula (I).

WO 97/09311 discloses piperidine derivatives of similar structure. However, these compounds display a high lipophilicity.

Unless otherwise indicated the following definitions are set forth to illustrate and define the meaning and scope of the various terms used to describe the invention herein.

In this specification the term "lower" is used to mean a group consisting of one to seven, preferably of one to four carbon atom(s).

The term "alkyl" refers to a branched or straight chain monovalent alkyl radical of one to seven carbon atoms, preferably one to four carbon atoms, unless otherwise indicated. This term is further exemplified by such radicals as methyl, ethyl, n-propyl, isopropyl, n-butyl, s-butyl, t-butyl and the like.

The term "halogen" refers to fluorine, chlorine, bromine and iodine, with chlorine and fluorine being preferred.

The term "alkoxy-" refers to the group R'—O—, wherein R' is alkyl.

The term "alkylamino-" refers to the group HR'N—, wherein R' is alkyl.

The term "di-alkylamino" refers to the group R'R"N—, wherein R' and R" are alkyl.

The term "pharmaceutically acceptable salts" embraces salts of the compounds of formula (I) with inorganic or organic acids such as hydrochloric acid, hydrobromic acid, nitric acid, sulphuric acid, phosphoric acid, citric acid, formic acid, maleic acid, acetic acid, succinic acid, tartaric acid, methanesulphonic acid, p-toluenesulphonic acid and the like, which are non-toxic to living organisms.

In detail, the present invention refers to compounds of formula (I)

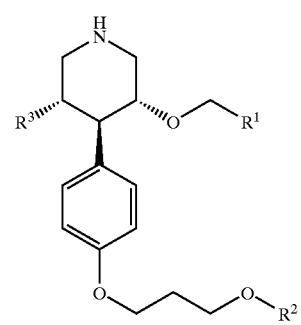

wherein

R¹ is naphthyl optionally substituted by one to three C₁–C₅-alkoxy groups;

R² is phenyl or benzyl, optionally substituted by substituents independently selected from one to three halogen, cyano, C₁–C₃-alkoxy and nitro groups;

R³ is hydroxymethyl, imidazolylmethyl, triazolylmethyl, H—[CH(OR⁴)]₂—CH₂—, or H—[CH(OR⁴)]₂—CH₂—O—CH₂—, or R³ᵃ—(CH₂)ₖ—[CH(OR⁴)]₁—CH₂—O—;

R³ᵃ is hydrogen, hydroxy, imidazolyl, triazolyl, C₁–C₃-alkoxy, C₁–C₃-alkoxy-C₂–C₃-alkoxy, hydroxy-C₂–C₃-alkoxy, C₁–C₃-alkylamino or C₁–C₃-dialkylamino;

R⁴ is hydrogen or C₁–C₃-alkyl;

k is 1 or 2, when R³ᵃ is hydrogen, k is 0;

l is 1 or 2; and pharmaceutically acceptable salts thereof.

The compounds of formula I have at least three asymmetric carbon atoms and can exist in the form of optically pure enantiomers, racemates, diastereomer mixtures, diastereomeric racemates, mixtures of diastereomeric racemates, in which the relative configuration of the three piperidine ring substitutents has to be all-trans as shown in formula I. The invention embraces all of these forms. Racemates, diastereomeric mixtures, diastereomeric racemates or mixtures of diastereomeric racemates can be separated according to usual methods, e.g. by column chromatography, thin-layer chromatography, HPLC and the like.

More particularly, the present invention relates to compounds of the above formula (I), wherein R¹ is naphthyl optionally substituted by one C₁–C₃-alkoxy group. In a more preferred embodiment R¹ is naphthyl substituted by one C₁–C₃-alkoxy group, preferably methoxy. In a further preferred embodiment, the alkoxy group is in meta position to the substituent providing the connection with the piperidine residue of the compounds of formula (I).

In a preferred embodiment, R² is benzyl substituted by one to three C₁–C₃-alkoxy groups or by one to three C₁–C₃-alkoxy groups in combination with one to three halogens. Preferably the benzyl group is substituted by one C₁–C₃-alkoxy or by one C₁–C₃-alkoxy group in combination with one to two halogens. The preferred $C_1$–$C_3$-alkoxy group is methoxy, the preferred halogen is fluorine. In a more preferred embodiment, the above mentioned alkoxy group is in ortho position to the substituent providing the connection with the phenylpiperidine of the compounds of formula (I).

In a preferred embodiment, the present invention comprises the above compounds wherein $R^{3a}$ is hydroxy or $C_1$–$C_3$-alkoxy.

Particularly, the invention relates to compounds wherein $R^3$ is $R^{3a}$—$(CH_2)_k$—$[CH(OR^4)]_1$—$CH_2$—O— or H—[CH$(OR^4)]_2$—$CH_2$—O—$CH_2$—.

In a preferred embodiment, the invention comprises the above compounds wherein 1 is 1.

More particularly, the invention relates to compounds wherein $R^3$ is $CH_3$—O—$CH_2$—$CH(OR^4)$—$CH_2$—O—, H—$[CH(OH)]_2$—$CH_2$—O—$CH_2$—, or HO—$CH_2$—CH$(OR^4)$—$CH_2$—O—.

Particularly, the invention relates to the above compounds wherein $R^4$ is hydrogen.

The invention especially discloses compounds of formula (I) and pharmaceutically acceptable salts thereof, selected from 1) (R)-1-methoxy-3-[(3S,4R,5R)-4-[4-[3-(2-methoxy-benzyloxy)-propoxy]-phenyl]-5-(4-methoxy-naphthalen-2-ylmethoxy)-piperidin-3-yloxy]-propan-2-ol;
2) (S)-1-methoxy-3-[(3S,4R,5R)-4-[4-[3-(2-methoxy-benzyloxy)-propoxy]-phenyl]-5-(4-methoxy-naphthalen-2-ylmethoxy)-piperidin-3-yloxy]-propan-2-ol;
3) (R)-1-[(3S,4R,5R)-4-[4-[3-(2-methoxy-benzyloxy)-propoxy]-phenyl]-5-(4-methoxy-naphthalen-2-ylmethoxy)-piperidin-3-yloxy]-3-(2-methoxy-ethoxy)-propan-2-ol;
4) (R)-1-[(3S,4R,5R)-4-[4-[3-(2-methoxy-benzyloxy)-propoxy]-phenyl]-5-(4-methoxy-naphthalen-2-ylmethoxy)-piperidin-3-yloxy]-3-methylamino-propan-2-ol;
5) 2-[3-[4-[(3S,4R,5R)-3-[(R)-2,3-dihydroxy-propoxy]-5-(4-methoxy-naphthalen -2-ylmethoxy)-piperidin-4-yl]-phenoxy]-propoxy]-benzonitrile;
6) 2-[3-[4-[(3S,4R,5R)-3-[(R)-2-hydroxy-3-methoxypropoxy]-5-(4methoxy-naphthalen-2-ylmethoxy)-piperidin-4-yl]-phenoxy]-propoxy]-benzonitrile;
7) 2-[3-[4-[(3S,4R,5R)-3-[(R)-2-hydroxy-3-(2-methoxy-ethoxy)-propoxy]-5-(4-methoxy-naphthalen-2-ylmethoxy)-piperidin-4-yl]-phenoxy]-propoxy]-benzonitrile;
8) (R)-3-[(3S,4R,5R)-5-(4-methoxy-naphthalen-2-ylmethoxy)-4-[4-[3-(2-nitro-phenoxy)-propoxy]-phenyl]-piperidin-3-yloxy]-propane-1,2-diol;
9) (R)-1-[(3S,4R,5R)-5-(4-methoxy-naphthalen-2-ylmethoxy)-4-[4-[3-(2-nitro-phenoxy)-propoxy]-phenyl]-piperidin-3-yloxy]-3-[1,2,4]triazol-1-yl-propan-2-ol;
10) (R)-1-imidazol-1-yl-3-[(3S,4R,5R)-5-(4-methoxy-naphthalen-2-ylmethoxy)-4-[4-[3-(2-nitro-phenoxy)-propoxy]-phenyl]-piperidin-3-yloxy)-propan-2-ol;
11) (R)-3-[(3S,4R,5R)-4-[4-[3-(5-fluoro-2-methoxy-benzyloxy)-propoxy]-phenyl]-5-(4-methoxy-naphthalen-2-ylmethoxy]-piperidin-3-yloxy]-propane-1,2-diol;
12) (R)-3-[(3S,4R,5R)-4-[4-[3-(2-chloro-phenoxy)-propoxy]-phenyl]-5-(4-methoxy-naphthalen-2-ylmethoxy)-piperidin-3-yloxy]-propane-1,2-diol;
13) (R)-3-[(3S,4R,5R)-4-[4-[3-(2-methoxy-benzyloxy)-propoxy]-phenyl]-5-(4-methoxy-naphthalen-2-ylmethoxy)-piperidin-3-ylmethoxy]-propane-1,2-diol;
14) (3S,4R,5R)-[4-[4-[3-(2-methoxy-benzyloxy)-propoxy]-phenyl]-5-(4-methoxy-naphthalen-2-ylmethoxy)-piperidin-3-yl]-methanol;
15) (3S,4R,5R)-3-imidazol-1-ylmethyl-4-[4-[3-(2-methoxy-benzyloxy)-propoxy]-phenyl]-5-(4-methoxy-naphthalen-2-ylmethoxy)-piperidine dihydrochloride;
16) (S)-3-[(3S,4R,5R)-4-[4-(3-benzyloxy-propoxy)-phenyl]-5-(naphthalen-2-ylmethoxy)-piperidin-3-ylmethoxy]-propane-1,2-diol;
17) (R)-3-[(3S,4R,5R)-4-[4-(3-benzyloxy-propoxy)-phenyl]-5-(naphthalen-2-ylmethoxy)-piperidin-3-ylmethoxy]-propane-1,2-diol;
18) (S)-3-[(3S,4R,5R)-4-[4-[3-(2-methoxy-benzyloxy)-propoxy]-phenyl]-5-(naphthalen-2-ylmethoxy)-piperidin-3-ylmethoxy]-propane-1,2-diol;
19) (R)-3-[(3S,4R,5R)-4-[4-[3-(2-methoxy-benzyloxy)-propoxy]-phenyl]-5-(naphthalen-2-ylmethoxy)-piperidin-3-ylmethoxy]-propane-1,2-diol;
20) (R)-1-[(3S,4R,5R)-4-[4-[3-(5-fluoro-2-methoxy-benzyloxy)-propoxy]-phenyl]-5-(4-methoxy-naphthalen-2-ylmethoxy)-piperidin-3-yloxy]-3-methoxy-propan-2-ol;
21) (R)-1-[(3S,4R,5R)-4-[4-[3-(3-fluoro-2-methoxy-benzyloxy)-propoxy]-phenyl]-5-(4-methoxy-naphthalen-2-ylmethoxy)-piperidin-3-yloxy]-3-methoxy-propan-2-ol;
22) (R)-1-[(3S,4R,5R)-4-[4-[3-(4-fluoro-2-methoxy-benzyloxy)-propoxy]-phenyl]-5-(4-methoxy-naphthalen-2-ylmethoxy)-piperidin-3-yloxy]-3-methoxy-propan-2-ol;
23) (R)-1-[(3S,4R,5R)-4-[4-[3-(4,5-difluoro-2-methoxy-benzyloxy)-propoxy]-phenyl]-5-(4-methoxy-naphthalen-2-ylmethoxy)-piperidin-3-yloxy]-3-methoxy-propan-2-ol;
24) (R)-1-[(3S,4R,5R)-4-[4-[3-(3,5-difluoro-2-methoxy-benzyloxy)-propoxy]phenyl]-5-(4-methoxy-naphthalen-2-ylmethoxy)-piperidin-3-yloxy]-3-methoxy-propan-2-ol; and 25) (R)-1-methoxy-3-[(3S,4R,5R)-4-[4-[3-(2-methoxy-benzyloxy)-propoxy]-phenyl]-5-(4-methoxy-naphthalen-2-ylmethoxy)-piperidin-3-ylmethoxy]-propan-2-ol.

An especially preferred compound is (R)-1-methoxy-3-[(3S,4R,5R)-4-[4-[3-(2-methoxy-benzyloxy)-propoxy]-phenyl]-5-(4-methoxy-naphthalen-2-ylmethoxy)-piperidin-3-yloxy]-propan-2-ol and pharmaceutically acceptable salts thereof.

A further especially preferred compound is (R)-3-[(3S,4R,5R)-4-[4-[3-(2-methoxy-benzyloxy)-propoxy]-phenyl]-5-(4-methoxy-naphthalen-2-ylmethoxy)-piperidin-3-ylmethoxy]-propane-1,2-diol and pharmaceutically acceptable salts thereof.

A further especially preferred compound is (R)-3-[(3S,4R,5R)-4-[4-[3-(5-fluoro-2-methoxy-benzyloxy)-propoxy]-phenyl]-5-(4-methoxy-naphthalen-2-ylmethoxy)-piperidin-3-yloxy]-propane-1,2-diol and pharmaceutically acceptable salts thereof.

A further especially preferred compound is (R)-1-[(3S, 4R,5R)-4-[4-[3-(5-fluoro-2-methoxy-benzyloxy)-propoxy]- phenyl]-5-(4-methoxy-naphthalen-2-ylmethoxy)-piperidin-3-yloxy]-3-methoxy-propan-2-ol and pharmaceutically acceptable salts thereof.

A further especially preferred compound is (R)-1-methoxy-3-[(3S,4R,5R)-4-[4-[3-(2-methoxy-benzyloxy)-propoxy]-phenyl]-5-(4-methoxy-naphthalen-2-ylmethoxy)-piperidin-3-ylmethoxy]-propan-2-ol and pharmaceutically acceptable salts thereof.

The invention also relates to pharmaceutical compositions comprising a compound as defined above and a pharmaceutically acceptable carrier and/or adjuvant. The pharmaceutical compositions may comprise in addition one or more compounds active against restenosis, glaucoma, cardiac infarct, high blood pressure and end organ damage, e.g. cardiac insufficiency and kidney insufficiency. Examples for these additional compounds are angiotensin converting enzyme-inhibitors, e.g. captopril, lisinopril, enalapril and cilazapril; angiotensin-(1)-receptor antagonists, e.g. lorsartan and valsartan; diuretica, e.g. hydrochlorothiazide, mefrusid and furosemid; endothelin receptor antagonists, e.g. bosentan; endothelin converting enzyme inhibitors or neutral endopeptidase inhibitors; calcium channel blockers (antagonists), e.g. nifedipine, verapamil, and diltiazem; nitrates, e.g. glyceroltrinitrates (nitroglycerin) and isosorbid-dinitrates; beta-receptor blockers, e.g. carvedilol, alprenolol and propranolol; alpha-1 adrenoceptor antagonists, e.g. prazosin and terazosin; and reserpin.

A further embodiment of the present invention refers to the use of a compound as defined above for the preparation of medicaments for the treatment or prophylaxis of restenosis, glaucoma, cardiac infarct, high blood pressure and end organ damage, e.g. cardiac insufficiency and kidney insufficiency.

An additional embodiment of the invention relates to a method for the prophylactic and/or therapeutic treatment of disorders in which renin plays a significant pathological role, especially restenosis, glaucoma, cardiac infarct, high blood pressure and end organ damage, e.g. cardiac insufficiency and kidney insufficiency which method comprises administering a compound as defined above to a human being or an animal.

The compounds as defined above may be manufactured by cleaving off the protecting group $P^1$ and optionally hydroxy protecting groups which may be present in compounds of formula (II)

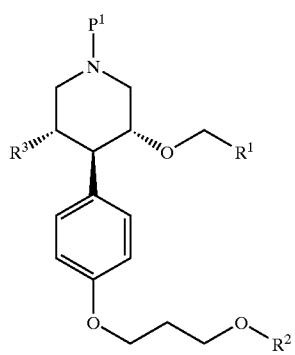

wherein $P^1$ represents a NH-protecting group and the remaining symbols have the significance given above wherein hydroxy groups which may be contained in $R^1$, $R^2$, and $R^3$ may optionally be present in protected form. If desired, reactive groups may be functionally modified in the thus-obtained compound of formula I (e.g. into esters) and/or converted into a pharmaceutically usable salt.

The cleavage of a protecting group $P^1$ and hydroxy protecting groups which may be present can be carried out in a manner known per se. Examples of protecting groups $P^1$ are usual amino protecting groups such as tert-butoxycarbonyl, benzyloxycarbonyl, allyloxycarbonyl, vinyloxycarbonyl, alkylsilylalkyloxycarbonyl such as 2-(trimethylsilyl)ethoxycarbonyl, and trichloroethoxycarbonyl. Examples of hydroxy protecting groups are ether-protecting groups such as tetrahydropyranyl, allyl, 2-(trimethylsilyl)ethoxymethyl, trityl, tert-butyldimethylsilyl or ester protecting groups such as acetyl. Examples of diol protecting groups are cyclic ether protecting groups such as isopropylidene or benzylidene.

The cleavage of these protecting groups is effected by acidic or basic hydrolysis, by reductive methods or by means of Lewis acids or fluoride salts. A solution of a mineral acid such as hydrochloric acid, hydrobromic acid, sulfuric acid, phosphoric acid and the like in an inert solvent or solvent mixture is advantageously used for the acidic hydrolysis. Suitable solvents are alcohols such as methanol or ethanol, ethers such as tetrahydrofuran or dioxan, chlorinated hydrocarbons such as methylene chloride, and the like. Alkali metal hydroxides and alkali metal carbonates such as potassium hydroxide or sodium hydroxide or potassium carbonate or sodium carbonate, organic amines such as piperidine, and the like can be used for the basic hydrolysis. Inert organic solvents as referred to above for the acidic hydrolysis can be used as solubilizers. The reaction temperature for the acidic and basic hydrolysis can be varied in a range from 0° C. to the reflux temperature, with the reaction preferably being carried out at between about 0° C. and room temperature. The tert-butoxycarbonyl group is conveniently cleaved off with hydrochloric acid, hydrogen chloride, trifluoroacetic acid or formic acid in the presence or absence of an inert solvent. Furthermore, the tert-butoxycarbonyl group can be cleaved off by means of anhydrous zinc bromide in the presence of an inert solvent, preferably methylene chloride. The cleavage of the trichloroethoxycarbonyl group can be advantageously effected reductively with zinc in glacial acetic acid. The reaction temperature can lie in a range of 0° C. to 40° C., with the reaction preferably being carried out at room temperature. The cleavage of the 2-(trimethylsilyl)ethoxycarbonyl group can be effected by means of fluoride ions in the presence of an inert solvent such as acetonitrile, dimethyl sulphoxide, dimethylformamide or tetrahydrofuran, preferably by means of tetrabutylammonium fluoride in tetrahydrofuran, at temperatures from about 0° C. to about room temperature.

The compounds of formula (II) are novel and are also an object of the invention. Their preparation is described in more detail hereinafter in Schemes 1–4 and in the Examples.

Scheme 1:

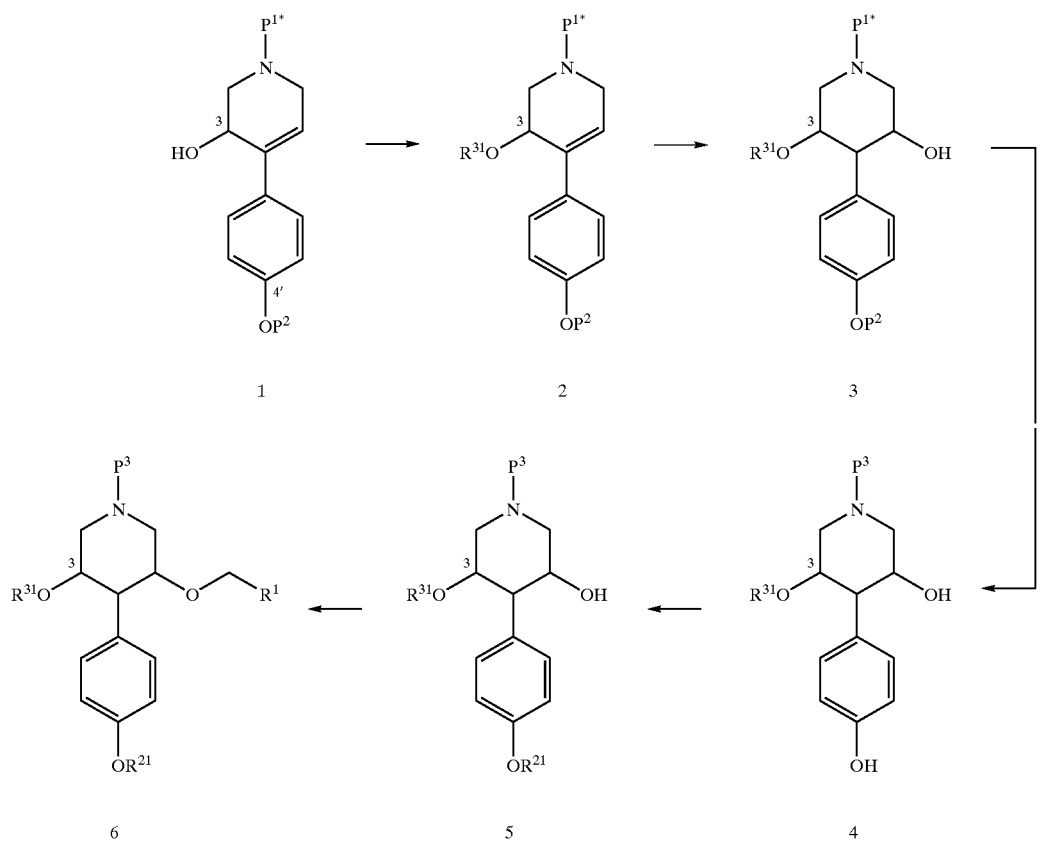

Derivatives of general formula 2 in which $P^{1*}$ has, in addition to the meanings of $P^1$, the meaning of benzyl or (R)— or (S)-2-phenethyl, can be obtained by alkylation of the 3-hydroxy function in a suitably N,4'-O-di-protected 4-(4-hydroxy-phenyl)-1,2,3,6-tetrahydro-pyridin-3-ol of the general formula 1. The alkylation can be performed in solvents as ethers, like tetrahydrofuran and 1,2-dimethoxyethane, N,N-dimethylformamide or dimethylsulfoxide with aliphatic chlorides, bromides, iodides, tosylates or mesylates in the presence of a base like sodium hydride or potassium tert-butoxide. The alkylating agents used can contain optionally suitably protected functional groups which allow further structural modifications at a later stage of the synthesis. Hydroboration of the ether compounds formed (general formula 2) followed by subsequent basic oxidative working-up produces compounds of the general formula 3 with high diastereoselectivity, the isomer bearing only equatorial substituents at the piperidine ring being formed almost exclusively. The absolute stereochemistry at carbon 3 of the piperidine ring remains unaffected during the transformation of compounds 1 to compounds 3. The hydroboration can be effected according to methods known per se, for example in a solvent which is inert under the reaction conditions, such as an ether, e.g. 1,2-dimethoxyethane, at a temperature between about 0° C. and 70° C., and with a diborane-containing or diborane-liberating reagent such as e.g. borane in tetrahydrofuran or a mixture of sodium borohydride and boron trifluoride etherate. The carboboranes which are formed as intermediates can be converted into the secondary alcohols of general formula 3 by reaction with bases, e.g. potassium hydroxide, and an oxidizing agent, e.g. hydrogen peroxide, at a temperature between about room temperature and 120° C. Removal of the N— and O— protective functions and reintroduction of a optionally different N-protective group ($P^3$), e.g. a N-Boc group, by well established procedures as e.g.: hydrogenolysis with hydrogen in the presence of a palladium catalyst followed by introduction of the Boc group with di-tert-butyldicarbonate in dioxan/water converts compounds of the general formula 3 into a compound of the general formula 4 bearing a phenolic and an aliphatic OH-function which can be derivatized selectively.

Selective derivatization of the phenolic function in compounds of general formula 4 can be performed by alkylation reactions using aliphatic chlorides, bromides, iodides, tosylates or mesylates in the presence of a base like potassium carbonate in solvents such as an ether like tetrahydrofuran, in N,N-dimethylformamide, dimethylsulfoxide, acetone, methyl-ethyl-ketone, or pyridine at temperatures between 0° C. and 140° C. leading to compounds of the general formula 5. The substituent introduced can function as a protecting group, being e.g. an allyl ether, or can be a unit which contains optionally suitably protected functional groups to allow further structural modifications at a later stage of the synthesis or consist of the whole substituent desired. Derivatization at the secondary hydroxy function of the piperidine ring can than be performed in solvents as ethers, like tetrahydrofuran or 1,2-dimethoxyethane, or in N,N- dimethylformamide or dimethylsulfoxide in the presence of an anion-forming base, like sodium hydride or potassium tert-butoxide, and a suitable alkylating agent, preferentially an aryl methyl chloride, bromide, mesylate or tosylate at temperatures between 0° C. and 40° C. thus giving compounds of the general formula 6. If $R^{21}$ represents allyl, then this protective function can be replaced by a suitable substituent at any stage of the synthesis, e.g. by treatment with a palladium catalyst as palladium-II-acetate in the presence of triphenylphosphine and lithiumborohydride in a solvent like tetrahydrofuran or 1,2-dimethoxyethane followed by an alkylation procedure as described above.

solvent like pyridine. If an excess of tosyl chloride is used, a short reaction time can prevent the formation of substantial amounts of the undesired ditosylate. Treatment of the monotosylate with base, e.g. with sodium hydroxide in dimethylsulfoxide, affords the corresponding oxiran 8. Optionally, the oxiran 8 can be prepared from the corresponding diol in a one step procedure by using reagents as diethoxytriphenylphosphorane (DTPP) in a solvent like dichloromethane or tetrahydrofuran, ether or 1,2-dimethoxyethane at temperatures between 40° C. and 100° C. under essentially neutral conditions (P. L. Robinson; J. W. Kelly; S. A. Evans, J. R. Phosphorus and Sulfur 1986, 26, Scheme 2:

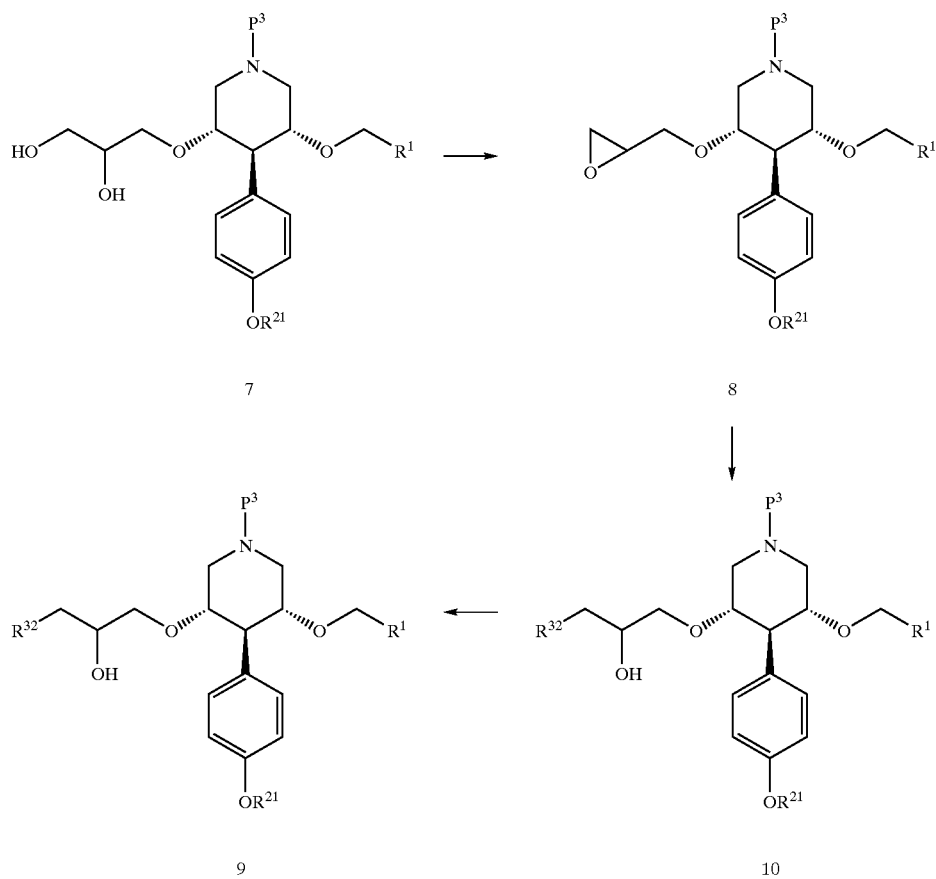

In case $R^{31}$ contains a diol function protected as 1,3-dioxolane derivative, then the free diol can be liberated using hydrochloric acid in methanol, a procedure which also liberates the secondary amino function of the piperidine ring, if protected with a Boc-protective group. The Boc-protective function can optionally be reintroduced using di-tert-butyl-dicarbonate in a solvent, like a mixture of water and dioxane, methanol or acetonitril, in the presence of a base, like sodium hydrogencarbonate or triethylamine, leading to compounds of the general formula 7. A primary/secondary diol unit can be modified by transformation of e.g. the primary hydroxy function into a leaving group, e.g. a tosyloxy- or a mesyloxy- group. Selective tosylation of a primary hydroxy function in the presence of a secondary hydroxy function can be performed with tosyl chloride in a 12–24). The oxiran opens regioselectively at the less hindered site when reacted with an alkali salt of an alcohol as methanol or methoxyethanol or an alkali salt of a heterocycle as [1,2,4]triazol or imidazol in a solvent like N,N-dimethylformamide, dimethylsulfoxide or an ether like tetrahydrofuran to give compounds of the general formula 9. Final removal of e.g. a Boc-protective group can be performed in the presence of acids such as hydrochloric, hydrobromic, sulfuric, phosphoric, trifluoroactic acid in a variety of solvents such as alcohols and alcohol/water mixtures, ethers and chlorinated hydrocarbons. The Boc-protective group can also be removed with anhydrous zinc bromide in inert solvents such as dichloromethane leading to compounds of the general formula 10.

Scheme 3:

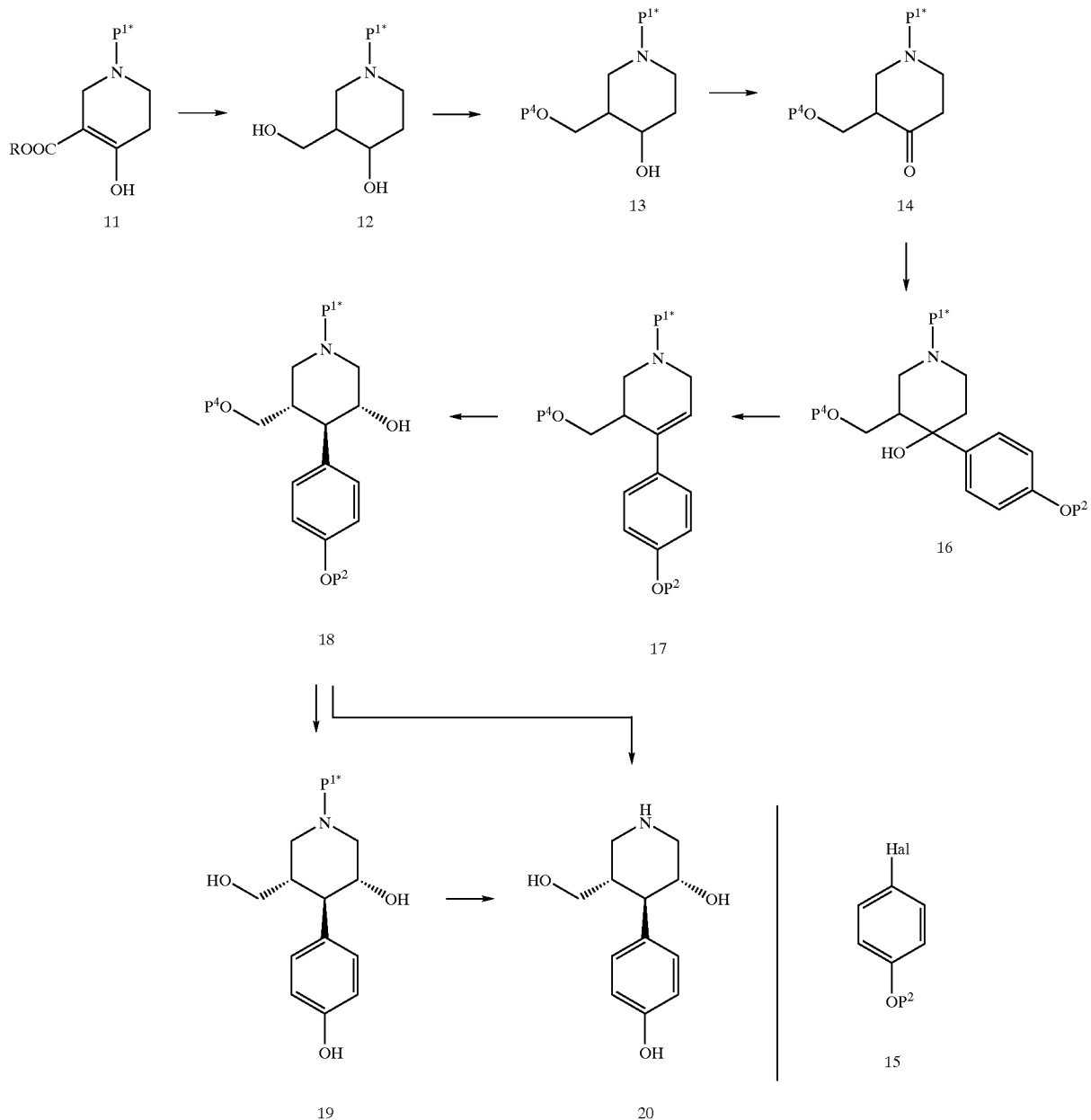

Derivatives of general formula 14 in which $P^{1*}$ has, in addition to the meanings of $P^1$, the meaning of benzyl can be obtained in accordance with Scheme 3 from the compound of general formula 11 (with R being e.g. methyl or ethyl; commercially available compounds, e.g. Aldrich) by reduction to the diol analogously to the process described by E. Jaeger and J. H. Biel in J. Org. Chem. 30(3), 740–744 (1965), followed by the introduction of a suitable protecting group for the primary alcohol, e.g. tert-butyldimethylsilyl, tert-butyldiphenylsilyl, preferably trityl. The oxidation of the secondary alcohol of general formula 13 can be carried out in manner known per se, e.g. by using oxalyl chloride and dimethyl sulphoxide as described by A. J. Mancuso and D. Swern in Synthesis 1981, 165, to yield the ketone of general formula 14.

Compounds of general formula 16 can be obtained by reacting compounds of general formula 14 in a manner known per se with metal-organic derivatives, preferably lithium or magnesium derivatives, prepared from compounds of general formula 15 wherein $P^2$ represents lower-alkoxy, preferably methoxy, or benzyloxy.

The reaction with such a metal-organic compound is effected according to methods known per se, for example in a solvent which is inert under the reaction conditions, such as an ether, at a temperature between about −78° C. and 75° C.

The compounds of general formula 17 can be obtained therefrom in the presence of an acid or another water-cleaving reagent, optionally in the presence of a base, in an organic solvent. As acids there come into consideration e.g. hydrochloric acid, trifluoroacetic acid or p-toluenesulphonic acid, and as the water-cleaving reagent there can be used e.g. phosphorus oxytrichloride in pyridine. The reaction temperature lies between 0–120° C.; as solvents there can be used e.g. toluene, dimethylformamide or alcohols.

Compounds of general formula 18 can be obtained from compounds of general formula 17 by hydroboration and subsequent basic oxidative working-up. The hydroboration can be effected according to methods known per se, for example in a solvent which is inert under the reaction conditions, such as an ether, e.g. 1,2-dimethoxyethane, at a temperature between about 0° C. and 70° C., and with a diborane-containing or diborane-liberating reagent such as e.g. borane in tetrahydrofuran or a mixture of sodium borohydride and boron trifluoride etherate. The carboboranes which are formed as intermediates can be converted into the secondary alcohols of general formula 18 by reaction with bases, e.g. potassium hydroxide, and an oxidizing agent, e.g. hydrogen peroxide, at a temperature between about room temperature and 120° C. Hydroboration of compounds of the general formula 17, followed by basic oxidative working-up produces compounds of the general formula 18 with high diastereoselectivity; the isomer bearing only equatorial substituents at the piperidine ring is almost exclusively formed.

Scheme 4:

Compounds of formula 18 in which $P^2$ is lower-alkoxy can be converted into compounds of general formula 19 by an alkyl-aryl ether cleavage. The ether cleavage is effected according to methods known per se by, preferably starting from compounds in which $P^2$ has the meaning methoxy, reacting the alkyl-aryl ether with mineral acids such as hydrobromic acid or hydroiodic acid or preferably with Lewis acids such as boron trichloride or boron tribromide in a solvent which is inert under the reaction conditions, such as e.g. a halogenated hydrocarbon, at a temperature between about −10° C. and room temperature. Under these conditions, the protecting group $P^4$ which, preferably, has the meaning trityl, tert-butyl-diphenylsilyl or tert-butyl-dimethylsilyl, is also cleaved.

Compounds of formula 19 in which $P^2$ is benzyl can be converted into compounds of general formula 20 by hydrogenolysis with hydrogen in the presence of a palladium catalyst in an inert solvent or solvent mixture. Suitable solvents are alcohols, such as methanol or ethanol, ethyl acetate and the like, at temperatures from about 0° C. to 40° C.

Compounds of formula 18 in which $P^2$ is benzyl, $P^1$ is benzyl and $P^4$ is trityl can directly be converted into compounds of general formula 20 by hydrogenolysis with hydrogen in the presence of a palladium catalyst under conditions mentioned above.

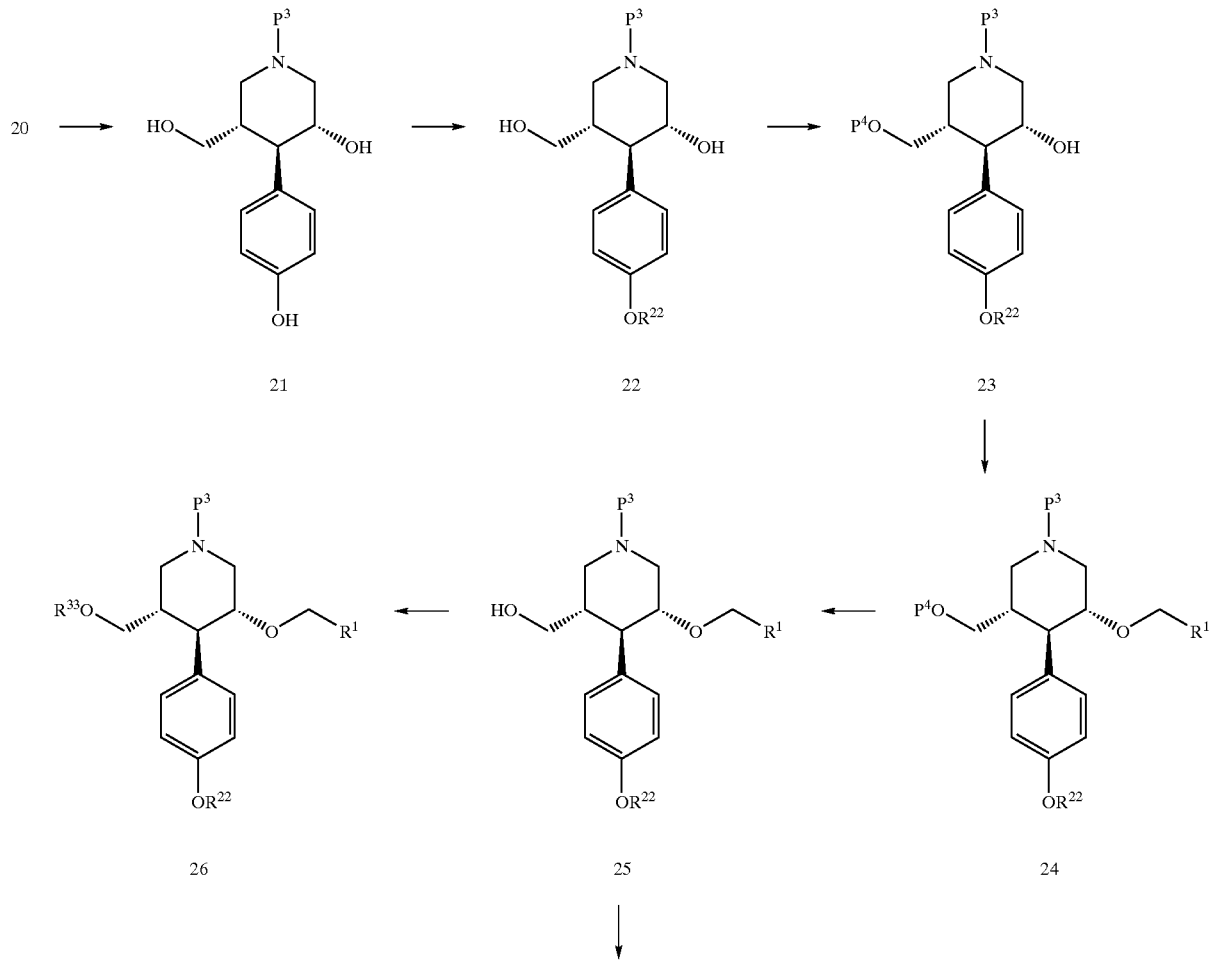

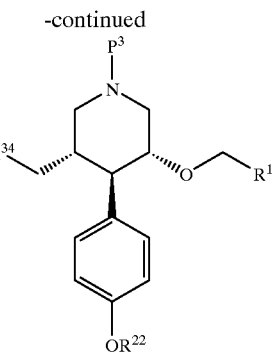

27

After removal of the N- and O-protecting functions compounds of formula 21 can be obtained by reintroduction of an optionally different N-protecting group, preferably tert-butoxycarbonyl, by well established procedures. The introduction of tert-butoxycarbonyl can be selectively effected by the reaction of compounds of general formula 20 with di-tert-butyldicarbonate in dioxan/water at temperatures from about −10° C. to room temperature.

Compounds of general formula 21 can be used as starting materials for the preparation of compounds of general formula 22 in which $R^{22}$ is the group —$(CH_2)_3$—O—$R^2$ with the meanings referred to above. The linkage of the group —$(CH_2)_3$—O—$R^2$ can be effected selectively by reaction with a derivative of the group to be introduced which carries a suitable leaving group. The selective linkage with the phenolic alcohol is effected according to alkylation methods which are known per se in the presence of a base such as potassium carbonate. Chlorides, bromides, iodides, tosylates or mesylates come into consideration as alkylating agents. The reaction is effected in a solvent which is inert under the reaction conditions, such as e.g. an ether such as tetrahydrofuran or an aromatic hydrocarbon such as e.g. toluene, pyridine, acetone or methyl ethyl ketone, at a temperature between about 0° C. and 100° C.

Compounds of general formula 23 can be obtained by introduction of a protecting group $P^4$ selective for primary alcohols and selectively cleavable at an appropriate later stage of the reaction sequence in presence of the N-protecting group and the other functionalities. Examples of such hydroxy protecting groups are tert-butyldimethylsilyl, tert-butyldiphenylsilyl, and preferably trityl.

Compounds of general formula 24 can be obtained from 23 by alkylation with a compound which yields the group —$CH_2$—$R^1$. The alkylation of the secondary alcohol is effected according to methods known per se, for example in a solvent which is inert under the reaction conditions, such as an ether, e.g. tetrahydrofuran or 1,2-dimethoxyethane, or dimethylformamide, with the aid of an alcoholate-forming base, e.g. sodium hydride, at a temperature between about 0° C. and 40° C. and using a halide, preferably chloride or bromide, or a sulfonic acid ester, e.g. a mesylate or tosylate, as the compound which yields the group —$CH_2$—$R^1$.

Compounds of general formula 25 can be obtained from 24 by selective cleavage of protecting group $P^4$. The cleavage of these protecting groups is effected by acidic hydrolysis or by means of Lewis acids. The trityl group is conveniently cleaved off with a mixture of trifluoroacetic acid and trifluoroacetic acid anhydride in the presence of an inert solvent, preferably dichloromethane in a very short time at temperatures from about −10° C. to 0° C. The cleavage of the silyl protecting groups can be effected by means of fluoride ions in the presence of an inert solvent such as acetonitril, dimethylsulphoxide, N,N-dimethylformamide or tetrahydrofuran, preferably by means of tetrabutylammonium fluoride in tetrahydrofuran, at temperatures from about 0° C. to about room temperature.

Compounds of general formula 26 can be obtained from 25 by alkylation with a compound which yields the group $R^{33}$, where $R^{33}$ has the meaning of H—[CH(OR$^4$)]$_2$—$CH_2$—. The alkylation of the primary alcohol is effected according to methods known per se, for example in a solvent which is inert under the reaction conditions, such as an ether, e.g. tetrahydrofuran or 1,2-dimethoxyethane, or dimethylformamide, with the aid of an alcoholate-forming base, e.g. sodium hydride, at a temperature between about 0° C. and 40° C. and using a halide, preferably chloride or bromide, or a sulfonic acid ester, e.g. a mesylate or tosylate, as the compound which yields the group $R^{33}$. Optionally, the alkylating agents used can contain suitably protected functional groups which allow further structural modifications at a later stage of the reaction sequence. As alkylating agent there comes into consideration e.g. allylbromide which then can be hydroxylated according to methods known per se, or (R)-(−)-2,2-dimethyl-4-(hydroxymethyl)-[1,3]dioxolane-p-toluenesulfonate. In case the diol function is protected as a 1,3-dioxolane derivative, then the free diol can be liberated using hydrochloric acid in methanol, a procedure which also liberates the secondary amino function of the piperidine ring, if protected by a Boc-group. The Boc-protective function can optionally be reintroduced using di-tert-butyl-dicarbonate in a solvent, like a mixture of water and dioxane, methanol or acetonitril, in the presence of a base, like sodium hydrogencarbonate or triethylamine. The resulting primary/secondary diol unit can be manipulated analogously as described for compounds of the general formula 8, 9 and 10.

Compounds of general formula 27 in which $R^{34}$ is imidazolyl or triazolyl can be obtained from compounds of general formula 25. The reaction is effected according to methods known per se, for example in a solvent which is inert under the reaction conditions, such as an ether, e.g. tetrahydrofuran or 1,2-dimethoxyethane, or N.N-dimethylformamide, with the aid of an anion-forming base, e.g. sodium hydride, at a temperature between about 0° C. and 40° C. and using a sulfonic acid ester, e.g. a tosylate, mesylate or triflate, as the activated derivative of the primary alcohol.

Compounds of general formula 27 where $R^{34}$ has the meaning of H—[CH(OR$^4$)]$_2$— can be obtained by transforming compounds of general formula 25 into the corresponding halides, preferably into chlorides or bromides, reacting them with metallorganic reagents according to methods known per se, e.g. with vinylmagnesium bromide in an inert solvent like tetrahydrofuran, and hydroxylating them according to methods known per se.

Piperidines of general formula 25, 26 and 27 can also be obtained in optically pure form. Separation into antipodes can be effected according to methods known per se, preferably at an early stage of the synthesis by salt formation with an optically active acid. For example, compounds of general formula 18 in which $P^{1*}$ has the meaning of benzyl can be obtained in their optically pure form by treatment with (+)- or (−)-mandelic acid and separation of the diastereomeric salts by fractional crystallization. Or, at a later stage, by derivatization with a chiral auxiliary substance such as, for example, (+)- or (−)-camphamoyl chloride and separation of the diastereomeric products by chromatography and/or crystallization and subsequent cleavage of the bond to the chiral auxiliary substance. In order to determine the absolute configuration of the piperidine derivative obtained, the pure diastereomeric salts and derivatives can be analyzed by conventional spectroscopic methods, with X-ray spectroscopy on single crystals being an especially suitable method.

Starting compounds 1 are known in the art and may be prepared according to the methods described in WO97/09311 or according to a reaction wherein a compound of formula 28 or a salt thereof

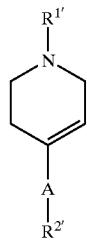

28 wherein A is arylene; $R^{1'}$ is —C*$R^{3'}R^{4'}R^{5'}$; $R^{2'}$ is —O-alkyl, —O-cycloalkyl, —O-alkenyl, or a group —OP$^2$ as defined above, —O-aryl, —O-aralkyl, —O-aralkoxyalkyl, —O-alkylsulfonyl, —O-arylsulfonyl, chlorine, bromine or iodine; $R^{3'}$ is hydrogen; $R^{4'}$ is aryl; $R^{5'}$ is alkyl, cycloalkyl, aryl, alkoxyalkyl or hydroxyalkyl; and, wherein C* is an asymmetric carbon atom; is epoxidated, optionally followed by isolation of the desired stereoisomer, resulting in a compound of formula 29

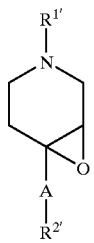

29

The reaction may be performed by transforming a compound of general formula 28 into a halohydrine which by treatment with base gives the epoxide of general formula 29.

In detail, examples for compounds which are known for use in such epoxidation reactions are halogens and organic bromo-compounds such as N-bromosuccinimide, dibromoisocyanurate and 1,3-dibromo-5,5-dimethylhydantoin. Preferred is bromine, especially in the presence of an acid, preferably HBr and chemical equivalents thereof. Inert solvents taken alone or in combination can be used, particularly, solvents which are known for their utilization in epoxidation reactions. Examples of such solvents are straight or cyclic ethers dimethylether, diethylether, tetrahydrofuran and monoglyme or diglyme alone or in such a combination that a sufficient miscibility with water is given. A preferred solvent is dioxane. Preferred is the above reaction in the presence of an acid. Examples of such acids are optically active or inactive acids such as the hydrohalic acids, sulfonic acids and H$_2$SO$_4$. Particularly preferred is HBr. In general the above reaction can be performed in a wide pH range. Preferred is a pH range from about 1 to 4 and particularly preferred is a pH range from about 1,5 to 3. A temperature range of from about −20° C. to the boiling point of the solvent is suitable for the reaction of the present invention. The preferred temperature range is between about −20° C. to about 20° C. preferably from about 0° C. to about 5° C.

The above reaction is followed by addition of a base such as NaOH, KOH, or a nitrogen-base such as triethylamine. Preferred is the use of NaOH or KOH. The temperature range for the addition of the base is between −20° C. and the boiling point of the solvent. Preferred is a temperature range between −20° C. and 20° C. Particularly preferred is the addition of the base between 0° C. and 5° C. In case the epoxidising agent reacts with a compound of the formula 28 without addition of an acid, the epoxide can be obtained without using a base.

According to the above process compounds of formula 29 are formed as a mixture of stereoisomers and particularly as a mixture of diastereomers, or only one of the diastereomers is formed. In a preferred aspect one of the diastereomers is formed preferably. Optionally the desired stereoisomer especially diastereomer can be isolated by methods known in the art such as crystallisation, chromatography or distillation, preferably crystallisation or chromatography. These methods also include the formation of salts or derivatives of compounds of the formula 29 and in a following step the separation of these salts or derivatives by the above methods. These methods, especially methods for the separation of diastereoisomers are well known in the art and are for example described in Houben-Weyl, Methods of Organic Chemistry (pp. Vol. E21, p. 81, 91).

Allylic alcohols of general formula 1 can be obtained from compounds of general formula 29 by rearrangement of the epoxide by a base. A preferred method is the reaction with a metal alcoholate such as potassium t-butoxide, aluminium isopropoxide, titanium (IV) t-butoxide, with a lithium amide such as lithium diisopropylamide or with an organolithium compound such as phenyllithium, sec-butyllithium or methyllithium to give a compound of the general formula 1.

Moreover, a preferred aspect of the above process is the reaction of a compound of the formula 29 or a salt thereof, with phenyllithium. Particularly preferred is the above reaction, wherein the desired stereoisomer of a compound of the formula 29 reacts with phenyllithium. Solvents for this reaction taken alone or in combination are for example: ethers such as tetrahydrofuran, diethyl ether, or tert-butyl methyl ether, aromatic hydrocarbons such as toluene or chlorobenzene or pyridine. The solvent, which is preferred, depends on the reagent. In the case of phenyllithium as the reagent, tert-butyl methyl ether is a particularly preferred solvent.

The rearrangement of the epoxide can be performed in a temperature range from about −40° C. up to the boiling of the solvent. Preferred is a temperature range from about −25° C. up to 0° C. Particularly preferred is a temperature of about −15° C.

The present invention relates to all compounds of formula (I), whenever prepared by one of the processes described above.

The invention also relates to compounds as defined above for the treatment of diseases which are associated with restenosis, glaucoma, cardiac infarct, high blood pressure and end organ damage, e.g. cardiac insufficiency and kidney insufficiency.

The compounds of formula I and their pharmaceutically usable salts have an inhibitory activity on the natural enzyme renin. The latter passes from the kidneys into the blood and there brings about the cleavage of angiotensinogen with the formation of the decapeptide angiotensin I which is then cleaved in the lungs, the kidneys and other organs to the octapeptide angiotensin II. Angiotensin II increases blood pressure not only directly by arterial constriction, but also indirectly by the liberation of the sodium ion-retaining hormone aldosterone from the adrenal gland, with which is associated an increase in the extracellular fluid volume. This increase is attributed to the action of angiotensin II itself or to that of the hepapeptide angiotensin III which is formed therefrom as a cleavage product. Inhibitors of the enzymatic activity of renin bring about a decrease in the formation of angiotensin I and as a consequence of this the formation of a smaller amount of angiotensin II. The reduced concentration of this active peptide hormone is the direct reason for the blood pressure-lowering activity of renin inhibitors.

The in-vitro potency of renin inhibitors can, as described by W. Fischli et al. in Hypertension, Vol. 18 (1), 22–31 (1991) or Hypertension Vol. 22 (1), 9–17 (1993) be demonstrated experimentally by means of the tests described hereinafter. The tests can be carried out in analogy to those described by D. T. Pals et al. in Hypertension Vol. 8, 1105–1112 (1986) or J. Boger et al. in J. Med. Chem. 28, 1779–1790 (1985) or J. F. Dellaria et al. in J. Med. Chem. 30,2137–2144 (1987) or T. Kokubu et al. in Biochem. Biophys. Res. Commun. 118, 929–933 (1984):

In vitro test with pure human renin:

The test is carried out in Eppendorf test tubes. The incubation mixture consists of (1) 100 µl of human renin in buffer A (0.1 M sodium phosphate solution, pH 7.4, containing 0.1% bovine serum albumin, 0.1% sodium azide and 1 mM ethylenediaminetetraacetic acid), sufficient for a renin activity of 2–3 ng of angiotensin I/ml/hr.; (2) 145 µl of buffer A: (3) 30 µl of 10 mM human tetradecapeptide renin substrate (hTD) in 10 mM hydrochloric acid: (4) 15 µl of dimethyl sulphoxide with or without inhibitor and (5) 10 µl of a 0.03 molar solution of hydroxyquinoline sulphate in water.

The samples are incubated for three hours at 37° C. and, respectively, 4° C. in triplicate. 2×100 µl samples per test tube are used in order to measure the production of angiotensin I via RIA (standard radioimmunoassay; clinical assay solid phase kit). Cross reactivities of the antibody used in the RIA are: angiotensin I 100%; angiotensin II 0.0013%; hTD (angiotensin I-Val-Ile-His-Ser-OH) 0.09%. The production of angiotensin I is determined by the difference between the test at 37° C. and that at 4° C.

The following controls are carried out:

(a) Incubation of hTD samples without renin and without inhibitor at 37° C. and 40° C. The difference between these two values gives the base value of the angiotensin I production.

(b) Incubation of hTD samples with renin, but without inhibitor at 37° C. and 4° C. The difference between these values gives the maximum value of the angiotensin I production.

In each sample the base value of the angiotensin I production is subtracted from the angiotensin I production which is determined. The difference between the maximum value and the base value gives the value of the maximum substrate hydrolysis (=100%) by renin.

The results are given as $IC_{50}$ values which denote the concentration of the inhibitor at which the enzymatic activity is inhibited by 50%. The $IC_{50}$ values are determined from a linear regression curve from a logit-log plot.

The results obtained in this test are compiled in the following Table:

TABLE

| Compound | $IC_{50}$ values in nMol/l |
|---|---|
| A | 0.06 |
| B | 0.03 |
| C | 0.08 |

TABLE-continued

| Compound | IC$_{50}$ values in nMol/l |
|---|---|
| D | 0.02 |
| E | 0.07 |

A = (R)-1-methoxy-3-[(3S,4R,5R)-4-[4-[3-(2-methoxy-benzyloxy)-propoxy]-phenyl]-5-(4-methoxy-naphthalen-2-ylmethoxy-piperidin-3-yloxy]-propan-2-ol;
B = (R)-1-[(3S,4R,5R)-4-[4-[3-(2-methoxy-benzyloxy)-propoxy]-phenyl]-5-(4-methoxy-naphthalen-2-ylmethoxy)-piperidin-3-yloxy]-3-(2-methoxy-ethoxy)-propan-2-ol;
C = (R)-3-[(3S,4R,5R)-5-(4-methoxy-naphthalen-2-ylmethoxy)-4-[4-[3-(2-nitro-phenoxy)-propoxy]-phenyl]-piperidin-3-yloxy]-propane-1,2-diol;
D = (3S,4R,5R)-[4-[4-[3-(2-methoxy-benzyloxy)-propoxy]-phenyl]-5-(4-methoxy-naphthalen-2-ylmethoxy)-piperidin-3-yl]-methanol; and
E = (3S,4R,5R)-3-imidazol-1-ylmethyl-4-[4-[3-(2-methoxy-benzyloxy)-propoxy]-phenyl]-5-(4-methoxy-naphthalen-2-ylmethoxy)-piperidine dihydrochloride.

It will be appreciated that the compounds of general formula (I) in this invention may be derivatised at functional groups to provide prodrug derivatives which are capable of conversion back to the parent compounds in vivo. Examples of such prodrugs include the physiologically acceptable and metabolically labile ester derivatives, such as methoxymethyl esters, methylthiomethyl esters and pivaloyloxymethyl esters. Additionally, any physiologically acceptable equivalents of the compounds of general formula (I), similar to the metabolically labile esters, which are capable of producing the parent compounds of general formula (I) in vivo, are within the scope of this invention.

As mentioned earlier, medicaments containing a compound of formula (I) are also an object of the present invention, as is a process for the manufacture of such medicaments, which process comprises bringing one or more compounds of formula (I) and, if desired, one or more other therapeutically valuable substances into a galenical administration form.

The pharmaceutical compositions may be administered orally, for example in the form of tablets, coated tablets, dragées, hard or soft gelatine capsules, solutions, emulsions or suspensions. Administration can also be carried out rectally, for example using suppositories; locally or percutaneously, for example using ointments, creams, gels or solutions; or parenterally, e.g. intravenously, intramuscularly, subcutaneously, intrathecally or transdermally, using for example injectable solutions. Furthermore, administration can be carried out sublingually or as opthalmological preparations or as an aerosol, for example in the form of a spray.

For the preparation of tablets, coated tablets, dragees or hard gelatine capsules the compounds of the present invention may be admixed with pharmaceutically inert, inorganic or organic excipients. Examples of suitable excipients for tablets, dragees or hard gelatine capsules include lactose, maize starch or derivatives thereof, talc or stearic acid or salts thereof.

Suitable excipients for use with soft gelatine capsules include for example vegetable oils, waxes, fats, semi-solid or liquid polyols etc.; according to the nature of the active ingredients it may however be the case that no excipient is needed at all for soft gelatine capsules.

For the preparation of solutions and syrups, excipients which may be used include for example water, polyols, saccharose, invert sugar and glucose.

For injectable solutions, excipients which may be used include for example water, alcohols, polyols, glycerine, and vegetable oils.

For suppositories, and local or percutaneous application, excipients which may be used include for example natural or hardened oils, waxes, fats and semi-solid or liquid polyols.

The pharmaceutical compositions may also contain preserving agents, solubilising agents, stabilising agents, wetting agents, emulsifiers, sweeteners, colorants, odorants, salts for the variation of osmotic pressure, buffers, coating agents or antioxidants. As mentioned earlier, they may also contain other therapeutically valuable agents.

It is a prerequisite that all adjuvants used in the manufacture of the preparations are non-toxic.

Intravenous, intramuscular or oral administration is a preferred form of use. The dosages in which the compounds of formula (I) are administered in effective amounts depend on the nature of the specific active ingredient, the age and the requirements of the patient and the mode of application. In general, daily dosages of about 1 mg–1000 mg, preferably 10 mg–300 mg, per day come into consideration.

The following Examples shall illustrate preferred embodiments of the present invention but are not intended to limit the scope of the invention.

EXAMPLES

Example 1

(R)-1-methoxy-3-[(3S,4R,5R)-4-[4-[3-(2-methoxy-benzyloxy)-propoxy]-phenyl]-5-(4-methoxy-naphthalen-2-ylmethoxy)-piperidin-3-yloxy]-propan-2-ol)

(a) 50.0 g (129.7 mmol) of (3S)-4-(4-benzyloxy-phenyl)-1-[(1R)-phenyl-ethyl]-1,2,3,6-tetrahydro-pyridin-3-ol were dissolved in 700 ml of N,N-dimethylformamide, treated portionwise with 41.5 g (about 1040 mmol) of sodium hydride dispersion in refined oil (55–65%) and the reaction mixture was stirred under argon for 1 hour. Then the mixture was treated portionwise with 153.1 g (519 mmol) of (R)-(−)-2,2-dimethyl-4-(hydroxymethyl)-[1,3]dioxolane-p-toluenesulfonate and stirred for two hours. Thereupon, the reaction mixture was poured into 2 liter of ice-water and extracted three times with 750 ml of ether. The combined ether phases were subsequently washed with water, dried over magnesium sulphate and evaporated on a rotary evaporator at a maximum 40° C. The residue which was thereby obtained was chromatographed on silica gel with methylenechloride/ethyl acetate (95/5). There were thus obtained 64.8 g (115 mmol), 88.7%, (3S)-4-(4-benzyloxy-phenyl)-3-[(4S)-2,2-dimethyl-[1,3]dioxolan-4-ylmethoxy]-1-[(R)-1-phenyl-ethyl]-1,2,3,6-tetrahydro-pyridine as light yellow solid; MS: 500 (M+H)$^+$.

(b) 29.4 g (58.8 mmol) of (3S)-4-(4-benzyloxy-phenyl)-3-[(4S)-2,2-dimethyl-[1,3]dioxolan-4-ylmethoxy]-1-[(R)-1-phenyl-ethyl]-1,2,3,6-tetrahydro-pyridine were dissolved in 175 ml of 1,2-dimethoxyethane, cooled to 5° C., treated with 235.4 ml of a 1.0 M solution of borane-tetrahydrofuran complex in tetrahydrofuran and stirred at room temperature for 5.5 hours. Then, the reaction mixture was again cooled to 5° C., treated slowly with 110 ml of water followed by 44.3 g (282 mmol) of sodium percarbonate. Subsequently, the reaction mixture was stirred at 50° C. for 17 hours. After cooling to room temperature the reaction solution was poured into 1.6 liters of water and extracted twice with 600 ml of dichloromethane each time. The combined dichloromethane phases were washed with water, dried over magnesium sulphate and evaporated on a rotary evaporator at a maximum 40° C.

The residue which was thereby obtained was chromatographed on silica gel with dichloromethane/ethyl acetate (8/2). There were thus obtained 23.1 g (44.6 mmol), 75.8%, (3R,4R,5S)-4-(4-benzyloxy-phenyl)-5-[(4S)-2,2-dimethyl-[1,3]dioxolan-4-ylmethoxy]-1-[(R)-1-phenyl-ethyl]-piperidin-3-ol as colorless solid; MS: 518 (M+H)$^+$.

(c) 19.2 g (37.1 mmol) (3R,4R,5S)-4-(4-benzyloxy-phenyl)-5-[(4S)-2,2-dimethyl-[1,3]dioxolan-4-ylmethoxy]-1-[(R)-1-phenyl-ethyl]-piperidin-3-ol dissolved in 200 ml methanol were hydrogenated in the presence of 3.84 g of palladium catalyst (10% on charcoal) for 23 hours. The reaction mixture was then filtered and evaporated yielding 12 g crude (3R,4R,5S)-5-[(4S)-(2,2-dimethyl-[1,3]dioxolan-4-ylmethoxy]-4-(4-hydroxy-phenyl)-piperidin-3-ol as colorless solid; MS: 324.3 (M+H)$^+$.

(d) 26.4 g (81.6 mmol) crude (3R,4R,5S)-5-[(4S)-(2,2-dimethyl-[1,3]dioxolan-4-ylmethoxy]-4-(4-hydroxy-phenyl)-piperidin-3-ol were dissolved in 160 ml dioxane/50 ml water and treated with 20 g (90 mmol) di-tert.-butyldicarbonate and 14.4 g (171 mmol) sodium hydrogencarbonate. The reaction mixture was then stirred for 1 hour. 150 ml 2N NaOH were then added and the mixture again stirred for an additional 30 minutes. It was then acidified to pH 7 with 130 ml 2N HCl solution. Thereafter, the reaction mixture was diluted with 500 ml of water extracted 3 times with 500 ml of dichloromethane, the organic phases were washed twice with distilled water, then dried over magnesium sulphate, filtered and concentrated in a water-jet vacuum. The thus-obtained crude product was chromatographed on silica gel with dichloromethane/ethyl acetate (7/3). There were thus obtained 29.4 g (69.4 mmol), 85% (3S,4R,5R)-3-[(4S)-(2,2-dimethyl-[1,3]dioxolan-4-ylmethoxy]-5-hydroxy-4-(4-hydroxy-phenyl)-piperidine-1-carboxylic acid tert-butyl ester as light brown oil; MS: 424.3 (M+H)$^+$.

(e) A solution of 18 g (42.5 mmol) of (3S,4R,5R)-3-[(4S)-(2,2-dimethyl-[1,3]dioxolan-4-ylmethoxy]-5-hydroxy-4-(4-hydroxy-phenyl)-piperidine-1-carboxylic acid tert-butyl ester in 120 ml of N,N-dimethylformamide was treated in succession with 13.6 g (63.8 mmol) of 1-(3-chloro-propoxymethyl)-2-methoxy-benzene (WO 97/09311) and 8.8 g (63.8 mmol) of potassium carbonate. This mixture was stirred at 120° C. for 16 hours. Subsequently, it was filtered, concentrated to a few milliliters, poured into 800 ml of an ice/water mixture and extracted three times with 300 ml of ether each time. The combined organic phases were washed once with a small amount of water, dried over magnesium sulphate, evaporated under reduced pressure and dried in a high vacuum. The thus-obtained crude product was separated on silica gel using a mixture of dichloromethane/ethyl acetate (7/3) as the eluent and yielded 24.5 g (40.6 mmol), 95.6%, (3S,4R,5R)-3-[(4S)-(2,2dimethyl-[1,3]dioxolan-4-ylmethoxy]-5-hydroxy-4-[4-[3-(2-methoxy-benzyloxy)-propoxy]phenyl]-piperidine-1-carboxylic acid tert-butyl ester as slightly yellow oil; MS: 602.3 (M+H)$^+$.

(f) 24.5 g (40.6 mmol) of (3S,4R,5R)-3-[(4S)-(2,2-dimethyl-[1,3]dioxolan-4-ylmethoxy]-5-hydroxy-4-[4-[3-(2-methoxy-benzyloxy)-propoxy]-phenyl]-piperidine-1-carboxylic acid tert-butyl ester and 12.6 g (60.9 mmol) of 3-chloromethyl-1-methoxy-naphthalene[example 1) (α)] were dissolved in 150 ml of N,N-dimethylformamide under argon and then 6.50 g (162 mmol) of sodium hydride dispersion (55% in mineral oil) was added. Subsequently, the mixture was stirred at room temperature for 1.5 hours. The reaction mixture was poured into 600 ml of ice-water, the product was extracted 3 times with 300 ml of ether, the organic phases were washed twice with distilled water, then dried over magnesium sulphate, filtered and concentrated in a water-jet vacuum. The thus-obtained crude product was chromatographed on silica gel using a mixture of dichloromethane/ethyl acetate (95/5) as the eluent and yielded 28.5 g (36.9 mmol), 90.9%, (3S,4R,5R)-3-[(4S)-2,2-dimethyl-[1,3]dioxolan-4-ylmethoxy]-4-[4-[3-(2-methoxy-benzyloxy)-propoxy]-phenyl]-5-(4-methoxy-naphthalen-2-ylmethoxy)-piperidine-1-carboxylic acid tert-butyl ester as colorless oil; MS: 772.5 (M+H)$^+$.

(g) 28.5 g (36.9 mmol) of (3S,4R,5R)-3-[(4S)-2,2-dimethyl-[1,3]dioxolan-4-ylmethoxy]-4-[4-[3-(2-methoxy-benzyloxy)-propoxy]-phenyl]-5-(4-methoxy-naphthalen-2-ylmethoxy)-piperidine-1-carboxylic acid tert-butyl ester were dissolved in 150 ml of abs. methanol at 0° C., then 118 ml (236 mmol) of hydrochloric acid in methanol (2.0 molar) were added dropwise at 5° C. max. and thereafter the mixture was warmed to room temperature. After 22 hours the reaction mixture was poured into ice-cold sodium hydrogen carbonate solution (1 l, 60 g sodium hydrogencarbonate) and the product was extracted three times with 500 ml dichloromethane, the organic phases were washed with distilled water, then dried over magnesium sulphate, filtered and concentrated in a water-jet vacuum. There were thus obtained 20.9 g (33.1 mmol), 90%, (R)-3-[(3S,4R,5R)-4-[4-[3-(2-methoxy-benzyloxy)-propoxy]-phenyl]-5-(4-methoxy-naphthalen-2-ylmethoxy)-piperidin-3-yloxy]-propane-1,2-diol as colorless oil; MS: 632.4 (M+H)$^+$.

(h) 20.9 g (33.1 mmol) of (R)-3-[(3S,4R,5R)-4-[4-[3-(2-methoxy-benzyloxy)-propoxy]-phenyl]-5-(4-methoxy-naphthalen-2-ylmethoxy)-piperidin-3-yloxy]-propane-1,2-diol were dissolved in 357 ml dioxane/178 ml water and treated with 7.6 g (35.0 mmol) di-tert.-butyldicarbonate and 6.3 g (74.7 mmol) sodium hydrogencarbonate. The reaction mixture was then stirred for 1 hour. 150 ml 2 N NaOH were then added and the mixture again stirred for an additional 30 minutes. It was then acidified to pH 7 with 130 ml 2N HCl solution. Thereafter, the reaction mixture was diluted with 600 ml of water extracted 3 times with 500 ml of dichloromethane, the organic phases were washed twice with distilled water, then dried over magnesium sulphate, filtered and concentrated in a water-jet vacuum. The thus-obtained crude product was chromatographed on silica gel with dichloromethane/methanol (10/0 to 9/1). There were thus obtained 23.7 g (32.3 mmol), 97.6%, (3S,4R,5R)-3-[(2R)-2,3-dihydroxy-propoxy]-4-[4-[3-(2-methoxy-benzyloxy)-propoxy]-phenyl]-5-(4-methoxy-naphthalen-2-ylmethoxy)-piperidine-1-carboxylic acid tert-butyl ester as colorless oil; MS:732.5 (M+H)$^+$.

(i) 23.65 g (32.3 mmol) of (3S,4R,5R)-3-[(2R)-2,3-dihydroxy-propoxy]-4-[4-[3-(2-methoxy-benzyloxy)- propoxy]-phenyl]-5-(4-methoxy-naphthalen-2-ylmethoxy)-piperidine-1-carboxylic acid tert-butyl ester were dissolved in 118 ml pyridine and treated while stirring rapidly with 31.1 g (162 mmol) toluol-4-sulfochlorid. After 15 minutes stirring at room temperature, 140 ml of water and 140 ml of tetrahydrofuran were added and stirring continued for additional 40 minutes. Thereafter, the reaction mixture was diluted with 1 l of water extracted 3 times with 500 ml of dichloromethane, the organic phases were washed three times with 400 ml 1N HCl solution and twice with distilled water, then dried over magnesium sulphate, filtered and concentrated in a water-jet vacuum. The thus-obtained crude product was chromatographed on silica gel with dichloromethane/ethyl acetate (9/1) giving 21.2 g of a mixture of the primary and the secondary tosylate. Separation on an HPLC silica gel column using hexane/isopropanol as eluent yielded 18.5 g (20.9 mmol), 64.6%(3S,4R,5R)-3-[(2S)-2-hydroxy-3-(toluene-4-sulfonyloxy)-propoxy]-4-[4-[3-(2-methoxy-benzyloxy)-propoxy]-phenyl]-5-(4-methoxy-naphthalen-2-ylmethoxy)-piperidine-1-carboxylic acid tert-butyl ester as colorless oil [MS: 886.4 (M+H)$^+$] and 1.3 g (1.47 mmol), 4.5% (3S,4R,5R)-3-[(2R)-3-hydroxy-2-(toluene-4-sulfonyloxy)-propoxy]-4-[4-[3-(2-methoxy-benzyloxy)-propoxy]-phenyl]-5-(4-methoxy-naphthalen-2-ylmethoxy)-piperidine-1-carboxylic acid tert-butyl ester as colorless oil; MS: 886.4 (M+H)$^+$.

(j) 18.5 g (20.9 mmol) of (3S,4R,5R)-3-[(2S)-2-hydroxy-3-(toluene-4-sulfonyloxy)-propoxy]-4-[4-[3-(2-methoxy-benzyloxy)-propoxy]-phenyl]-5-(4-methoxy-naphthalen-2-ylmethoxy)-piperidine-1-carboxylic acid tert-butyl ester were dissolved in 530 ml dimethylsulfoxid and treated while stirring at room temperature with 90.7 ml (454 mmol) 5M sodium hydroxide solution. The reaction mixture was then stirred for 1 hour, diluted with 800 ml of water and extracted twice with 400 ml of ether. The organic phases were washed twice with distilled water, then dried over magnesium sulphate, filtered and concentrated in a water-jet vacuum. There were thus obtained 14.7 g (20.6 mmol), 99% (3R,4R,5S)-4-[4-[3-(2-methoxy-benzyloxy)-propoxy]-phenyl]-3-(4-methoxy-naphthalen-2-ylmethoxy)-5-[(2R)-oxiranylmethoxy]-piperidine-1-carboxylic acid tert-butyl ester as colorless oil; MS: 714.3 (M+H)$^+$.

(k) 14.7 g (20.6 mmol) of (3R,4R,5S)-4-[4-[3-(2-methoxy-benzyloxy)-propoxy]-phenyl]-3-(4-methoxy-naphthalen-2-ylmethoxy)-5-[(2R)-oxiranylmethoxy]-piperidine-1-carboxylic acid tert-butyl ester were dissolved in 98 ml N,N-dimethylformamide and treated at room temperature while stirring with 21.9 ml (118 mmol) 5.4M sodium methylate solution in methanol. The reaction mixture was then stirred for 16 hours, diluted with 400 ml of water and extracted twice with 300 ml of ether. The organic phases were washed twice with distilled water, then dried over magnesium sulphate, filtered and concentrated in a water-jet vacuum. There were thus obtained 15.3 g (20.5 mmol), 99.5% (3S,4R,5R)-3-[(2R)-2-hydroxy-3-methoxy-propoxy]-4-[4-[3-(2-methoxy-benzyloxy)-propoxy]-phenyl]-5-(4-methoxy-naphthalen-2-ylmethoxy)-piperidine-1-carboxylic acid tert-butyl ester as colorless oil; MS: 746.4 (M+H)$^+$.

(l) 15.3 g (20.5 mmol) of (3S,4R,5R)-3-[(2R)-2-hydroxy-3-methoxy-propoxy]-4-[4-[3-(2-methoxy-benzyloxy)-propoxy]-phenyl]-5-(4-methoxy-naphthalen-2-ylmethoxy)-piperidine-1-carboxylic acid tert-butyl ester were dissolved in 70 ml of abs. methanol at 0° C., then 118 ml (236 mmol) of hydrochloric acid in methanol (2.0 molar) were added dropwise at 5° C. max. and thereafter the mixture was warmed to room temperature. After 22 hours the reaction mixture was poured into ice-cold sodium hydrogen carbonate solution (1 l, 60 g sodium hydrogen carbonate) and the product was extracted three times with 500 ml dichloromethane, the organic phases were washed with distilled water, then dried over magnesium sulphate, filtered and concentrated in a water-jet vacuum. The thus-obtained crude product was chromatographed on silica gel with dichloromethane/methanol (95/5). There were thus obtained 9.3 g (14.4 mmol), 70.2%, (R)-1-methoxy-3-[(3S,4R,5R)-4-[4-[3-(2-methoxy-benzyloxy)-propoxy]-phenyl]-5-(4-methoxy-naphthalen-2-ylmethoxy)-piperidin-3-yloxy]-propan-2-ol as colorless oil; MS: 646.3 (M+H)$^+$.

Preparation of 3-chloromethyl-1-methoxy-naphthalene (a) 15.0 g (79.7 mmol) of (4-methoxy-naphthalen-2-yl)-methanol [Chem. Pharm. Bull. 19(6), 1245–1256 (1971)] were dissolved in 100 ml of dichloromethane, the solution treated with 20 ml of triethylamine, cooled to −5° C. and treated slowly with 9.3 ml (119.5 mmol) methanesulfonyl chloride. Then, the reaction mixture was stirred at room temperature for 23 hours, concentrated in a water-jet vacuum, redissolved in 80 ml of tetrahydrofuran, treated with 11.25 g of sodium hydrogen carbonate and stirred for another 2 hours. The suspension was then diluted with 500 ml of water and extracted three times with 300 ml of ethyl acetate, the organic phases were washed once with distilled water, then dried over magnesium sulphate, filtered and concentrated in a water-jet vacuum. The thus-obtained crude product was chromatographed on silica gel with pentane/dichloromethane (4/1). There were thus obtained 11.9 g (57.5 mmol), 72.5% 3-chloromethyl-1-methoxy-naphthalene as a colorless solid; MS: 206 (M)$^+$.

Example 2

(S)-1-methoxy-3-[(3S,4R,5R)-4-[4-[3-(2-methoxy-benzyloxy)-propoxy]-phenyl]-5-(4-methoxy-naphthalen-2-ylmethoxy)-piperidin-3-yloxy]-propan-2-ol (a) In analogy to the procedure described in example 1 (j) the (3S,4R,5R)-3-[(2R)-3-hydroxy-2-(toluene-4-sulfonyloxy)-propoxy]-4-[4-[3-(2-methoxy-benzyloxy)-propoxy]-phenyl]-5-(4-methoxy-naphthalen-2-ylmethoxy)-piperidine-1-carboxylic acid tert-butyl ester [example 1) (i)] was treated with sodium hydroxide in dimethylsulfoxide to yield the (3R,4R,5S)-4-[4-[3-(2-methoxy-benzyloxy)-propoxy]-phenyl]-3-(4-methoxy-naphthalen-2-ylmethoxy)-5-[(2S)-oxiranylmethoxy]-piperidine-1-carboxylic acid tert-butyl ester as colorless oil; MS: 714.3 (M+H)$^+$.

(b) In analogy to the procedure described in example 1 (k) the (3R,4R,5S)-4-[4-[3-(2-methoxy-benzyloxy)-propoxy]-phenyl]-3-(4-methoxy-naphthalen-2-ylmethoxy)-5-[(2S)-oxiranylmethoxy]-piperidine-1-carboxylic acid tert-butyl ester was treated with sodium methylate in N,N-dimethylformamide to yield the (3S,4R,5R)-3-[(2S)-2-hydroxy-3-methoxy-propoxy]-4-[4-[3-(2-methoxy-benzyloxy)-propoxy]-phenyl]-5-(4-methoxy-naphthalen-2- ylmethoxy)-piperidine-1-carboxylic acid tert-butyl ester as colorless oil; MS: 746.4 (M+H)$^+$.

(c) In analogy to the procedure described in example 1) (l) the (3S,4R,5R)-3-[(2S)-2-hydroxy-3-methoxy-propoxy]-4-[4-[3-(2-methoxy-benzyloxy)-propoxy]-phenyl]-5-(4-methoxy-naphthalen-2-ylmethoxy)-piperidine-1-carboxylic acid tert-butyl ester was deprotected with HCl in methanol to yield the (2S)-1-methoxy-3-[(3S,4R,5R)-4-[4-[3-(2-methoxy-benzyloxy)-propoxy]-phenyl]-5-(4-methoxy-naphthalen-2-ylmethoxy)-piperidin-3-yloxy]-propan-2-ol as colorless oil; MS: 646.3 (M+H)$^+$.

Example 3

(R)-1-[(3S,4R,5R)-4-[4-[3-(2-methoxy-benzyloxy)-propoxy]-phenyl]-5-(4-methoxy-naphthalen-2-ylmethoxy)-piperidin-3-yloxy]-3-(2-methoxy-ethoxy)-propan-2-ol (a) In analogy to the procedure described in example 1 (k) the (3R,4R,5S)-4-[4-[3-(2-methoxy-benzyloxy)-propoxy]-phenyl]-3-(4-methoxy-naphthalen-2-ylmethoxy)-5-[(2R)-oxiranylmethoxy]-piperidine-1-carboxylic acid tert-butyl ester was treated with sodium 2-methoxy-ethylate (prepared from 2-methoxy-ethanol and sodium hydride) to give the (3S,4R,5R)-3-[(2R)-2-hydroxy-3-(2-methoxy-ethoxy)-propoxy]-4-[4-[3-(2-methoxy-benzyloxy)-propoxy]-phenyl]-5-(4-methoxy-naphthalen-2-ylmethoxy)-piperidine-1-carboxylic acid tert-butyl ester as colorless oil; MS: 790.4 (M+H)$^+$.

(b) In analogy to the procedure described in example 1) (l) the (3S,4R,5R)-3-[(2R)-2-hydroxy-3-(2-methoxy-ethoxy)-propoxy]-4-[4-[3-(2-methoxy-benzyloxy)-propoxy]-phenyl]-5-(4-methoxy-naphthalen-2-ylmethoxy)-piperidine-1-carboxylic acid tert-butyl ester was deprotected with HCl in methanol to yield the (R)-1-[(3S,4R,5R)-4-[4-[3-(2-methoxy-benzyloxy)-propoxy]-phenyl]-5-(4-methoxy-naphthalen-2-ylmethoxy)-piperidin-3-yloxy]-3-(2-methoxy-ethoxy)-propan-2-ol as colorless oil; MS: 690.3 (M+H)$^+$.

Example 4

(R)-1-[(3S,4R,5R)-4-[4-[3-(2-methoxy-benzyloxy)-propoxy]-phenyl]-5-(4-methoxy-naphthalen-2-ylmethoxy)-piperidin-3-yloxy]-3-methylamino-propan-2-ol (a) 50 mg (0.070 mmol) (3R,4R,5S)-4-[4-[3-(2-methoxy-benzyloxy)-propoxy]-phenyl]-3-(4-methoxy-naphthalen-2-ylmethoxy)-5-[(2R)-oxiranylmethoxy]-piperidine-1-carboxylic acid tert-butyl ester were dissolved in 0.45 ml (3.6 mmol) 8.03 M solution of methylamine in ethanol. The reaction mixture was stirred for 16 hours at 70° C. in a dosed wessel. The reaction mixture was then concentrated in a water-jet vacuum and the thus-obtained crude product was chromatographed on silica gel with dichloromethane/methanol/sat. aq. ammonia (95/5/0.1). There were thus obtained 52.2 mg (0.049 mmol), 70% (3S,4R,5R)-3-[(2R)-2-hydroxy-3-methylamino-propoxy)-4-[4-[3-(2-methoxy-benzyloxy)-propoxy]-phenyl]-5-(4-methoxy-naphthalen-2-ylmethoxy)-piperidine-1-carboxylic acid tert-butyl ester as colorless oil; MS: 745.5 (M+H)$^+$.

(b) In analogy to the procedure described in example 1) (l) the (3S,4R,5R)-3-[(2R)-2-hydroxy-3-methylamino-propoxy)-4-[4-[3-(2-methoxy-benzyloxy)-propoxy]-phenyl]-5-(4-methoxy-naphthalen-2-ylmethoxy)-piperidine-1-carboxylic acid tert-butyl ester was deprotected with HCl in methanol to yield the (R)-1-[(3S,4R,5R)-[4-[3-(2-methoxy-benzyloxy)-propoxy]-phenyl]-5-(4-methoxy-naphthalen-2-ylmethoxy)-piperidin-3-yloxy]-3-methylamino-propan-2-ol as colorless oil; MS: 645.3 (M+H)$^+$.

Example 5

2-[3-[4-[(3S,4R,5R)-3-[(2R)-2,3-dihydroxy-propoxy]-5-(4-methoxy-naphthalen-2-ylmethoxy)-piperidin-4-yl]-phenoxy]-propoxy]-benzonitrile (a) 50.0 g (416 mmol) of 2-hydroxy-benzonitril and 101 g (499 mmol) of 1,3-dibromo-propane were dissolved in 450 ml of 2-butanone, 138 g (997 mmol) of potassium carbonate were then added and the reaction mixture stirred under reflux for 2 hours. After cooling to room temperature, the mixture was filtered and the filtrate concentrated in a water-jet vacuum. Thereafter 250 ml of ice-water were added and the product was extracted three times with 200 ml dichloromethane, the organic phases were washed with 10% of potassium carbonate solution followed by distilled water, then dried over magnesium sulphate, filtered and concentrated in a water-jet vacuum. The thus-obtained crude product crystallized, the crystals were filtered off and washed with hexane. There were thus obtained 44.8 g (187 mmol), 44.9% 2-(3-bromo-propoxy)-benzonitrile as colorless solid; MS: 239, 241 (M)$^+$.

(b) In analogy to the procedure described in example 1) (e) the (3S,4R,5R)-3-[(4S)-(2,2-dimethyl-[1,3]dioxolan-4-ylmethoxy]-5-hydroxy-4-(4-hydroxy-phenyl)-piperidine-1-carboxylic acid tert-butyl ester was treated with the 2-(3-bromo-propoxy)-benzonitrile to yield the (3S,4R,5R)-4-[4-[3-(2-cyano-phenoxy)-propoxy]-phenyl]-3-[(4S)-2,2-dimethyl-[1,3]dioxolan-4-ylmethoxy]-5-hydroxy-piperidine-1-carboxylic acid tert-butyl ester as colorless oil; MS: 583 (M+H)$^+$.

(c) In analogy to the procedure described in example 1) (f) the (3S,4R,5R)-4-[4-[3-(2-cyano-phenoxy)-propoxy]-phenyl]-3-[(4S)-2,2-dimethyl-[1,3]dioxolan-4-ylmethoxy]-5-hydroxy-piperidine-1-carboxylic acid tert-butyl ester was reacted with 3-chloromethyl-1-methoxy-naphthalene [example 1 (α)] to yield the (3S,4R,5R)-4-[4-[3-(2-cyano-phenoxy)-propoxy]-phenyl]-3-[(4S)-2,2-dimethyl-[1,3]dioxolan-4-ylmethoxy]-5-(4-methoxy-naphthalen-2-ylmethoxy)-piperidine-1-carboxylic acid tert-butyl ester as colorless oil; MS: 753 (M+H)$^+$.

(d) In analogy to the procedure described in example 1) (g) the (3S,4R,5R)-4-[4-[3-(2-cyano-phenoxy)-propoxy]-phenyl]-3-[(4S)-2,2-dimethyl-[1,3]dioxolan-4-ylmethoxy]-5-(4-methoxy-naphthalen-2-ylmethoxy)-piperidine-1-carboxylic acid tert-butyl ester was deprotected with HCl in methanol to yield the 2-[3-[4-[(3S,4R,5R)-3-[(2R)-2,3-dihydroxy-propoxy]-5-(4-methoxy-naphthalen-2-ylmethoxy)-piperidin-4-yl]-phenoxy]-propoxy]-benzonitrile as white foam; MS: 613 (M+H)$^+$.

Example 6

2-[3-[4-[(3S,4R,5R)-3-[(2R)-2-hydroxy-3-methoxy-propoxy]-5-(4-methoxy-naphthalen-2-ylmethoxy)-piperidin-4-yl]-phenoxy]-propoxy]-benzonitrile (a) In analogy to the procedure described in example 1 (h) the 2-[3-[4-[(3S,4R,5R)-3-[(2R)-2,3-dihydroxy-propoxy]-5-

(4-methoxy-naphthalen-2-ylmethoxy)-piperidin-4-yl]-phenoxy]-propoxy]-benzonitrile was treated with di-tert.-butyldicarbonate to yield the (3S,4R,5R)-4-[4-[3-(2-cyano-phenoxy)-propoxy]-phenyl]-3-[(2R)-2,3-dihydroxy-propoxy]-5-(4-methoxy-naphthalen-2-ylmethoxy)-piperidine-1-carboxylic acid tert-butyl ester as colorless oil; MS: 713 (M+H)⁺.

(b) In analogy to the procedure described in example 1) (i) the (3S,4R,5R)-4-[4-[3-(2-cyano-phenoxy)-propoxy]-phenyl]-3-[(2R)-2,3-dihydroxy-propoxy]-5-(4-methoxy-naphthalen-2-ylmethoxy)-piperidine-1-carboxylic acid tert-butyl ester was treated with toluol-4-sulfochlorid to yield the (3S,4R,5R)-4-[4-[3-(2-cyano-phenoxy)-propoxy]-phenyl]-3-[(2S)-2-hydroxy-3-(toluene-4-sulfonyloxy)-propoxy]-5-(4-methoxy-naphthalen-2-ylmethoxy)-piperidine-1-carboxylic acid tert-butyl ester as colorless foam; MS: 868 (M+H⁺)·

(c) In analogy to the procedure described in example 1) (j) the (3S,4R,5R)-4-[4-[3-(2-cyano-phenoxy)-propoxy]-phenyl]-3-[(2S)-2-hydroxy-3-(toluene-4-sulfonyloxy)-propoxy]-5-(4-methoxy-naphthalen-2-ylmethoxy)-piperidine-1-carboxylic acid tert-butyl ester was treated with sodium hydroxide solution in dimethylsulfoxide to yield the (3R,4R,5S)-4-[4-[3-(2-cyano-phenoxy)-propoxy]-phenyl]-3-(4-methoxy-naphthalen-2-ylmethoxy)-5-[(2R)-oxiranylmethoxy]-piperidine-1-carboxylic acid tert-butyl ester as colorless oil; MS: 695 (M+H)⁺.

(d) In analogy to the procedure described in example 1 (k) the (3R,4R,5S)-4-[4-[3-(2-cyano-phenoxy)-propoxy]-phenyl]-3-(4-methoxy-naphthalen-2-ylmethoxy)-5-[(2R)-oxiranylmethoxy]-piperidine-1-carboxylic acid tert-butyl ester was treated with sodium methoxide in N,N-dimethylformamide to yield the (3S,4R,5R)-4-[4-[3-(2-cyano-phenoxy)-propoxy]-phenyl]-3-[(2R)-2-hydroxy-3-methoxy-propoxy]-5-(4-methoxy-naphthalen-2-ylmethoxy)-piperidine-1-carboxylic acid tert-butyl ester as colorless foam; MS: 727 (M+H⁺).

(e) In analogy to the procedure described in example 1 (l) the (3S,4R,5R)-4-[4-[3-(2-cyano-phenoxy)-propoxy]-phenyl]-3-[(2R)-2-hydroxy-3-methoxy-propoxy]-5-(4-methoxy-naphthalen-2-ylmethoxy)-piperidine-1-carboxylic acid tert-butyl ester was deprotected with HCl in methanol to yield the 2-[3-[4-[(3S,4R,5R)-3-[(2R)-2-hydroxy-3-methoxy-propoxy]-5-(4-methoxy-naphthalen-2-ylmethoxy)-piperidin-4-yl]-phenoxy]-propoxy]-benzonitrile as colorless oil; MS: 627 (M+H)⁺.

Example 7

2-[3-[4-[(3S,4R,5R)-3-[(2R)-2-hydroxy-3-(2-methoxy-ethoxy)-propoxy]-5-(4-methoxy-naphthalen-2-ylmethoxy)-piperidin-4-yl]-phenoxy]-propoxy]-benzonitrile (a) In analogy to the procedure described in example 1 (k) the (3R,4R,5S)-4-[4-[3-(2-cyano-phenoxy)-propoxy]-phenyl]-3-(4-methoxy-naphthalen-2-ylmethoxy)-5-[(2R)-oxiranylmethoxy]-piperidine-1-carboxylic acid tert-butyl ester was treated with sodium 2-methoxy-ethylate (prepared from 2-methoxy-ethanol and sodium hydride) to give the (3S,4R,5R)-4-[4-[3-(2-cyano-phenoxy)-propoxy]-phenyl]-3-[(2R)-2-hydroxy-3-(2-methoxy-ethoxy)-propoxy]-5-(4-methoxy-naphthalen-2-ylmethoxy)-piperidine-1-carboxylic acid tert-butyl ester as colorless oil; MS: 771 (M+H)⁺.

(b) In analogy to the procedure described in example 1 (l) the (3S,4R,5R)-4-[4-[3-(2-cyano-phenoxy)-propoxy]-phenyl]-3-[(2R)-2-hydroxy-3-(2-methoxy-ethoxy)-propoxy]-5-(4-methoxy-naphthalen-2-ylmethoxy)-piperidine-1-carboxylic acid tert-butyl ester was deprotected with HCl in methanol to yield the 2-[3-[4-[(3S,4R, 5R)-3-[(2R)-2-hydroxy-3-(2-methoxy-ethoxy)-propoxy]-5-(4-methoxy-naphthalen-2-ylmethoxy)-piperidin-4-yl]-phenoxy]-propoxy]-benzonitrile as colorless foam; MS: 671 (M+H)⁺.

Example 8

(R)-3-[(3S,4R,5R)-5-(4-methoxy-naphthalen-2-ylmethoxy)-4-[4-[3-(2-nitro-phenoxy)-propoxy]-phenyl]-piperidin-3-yloxy]-propane-1,2-diol (a) In analogy to the procedure described in example 5) (a) 2-nitrophenol was treated with sodium carbonate followed by 1,3-dibromo-propane in N,N-dimethylformamide to yield the 1-(3-bromo-propoxy)-2-nitro-benzene as slightly green solid; MS: 259, 261 (M)⁺.

(b) In analogy to the procedure described in example 1) (e) the (3S,4R,5R)-3-[(4S)-(2,2-dimethyl-[1,3]dioxolan-4-ylmethoxy]-5-hydroxy-4-(4-hydroxy-phenyl)-piperidine-1-carboxylic acid tert-butyl ester was treated with the 1-(3-bromo-propoxy)-2-nitro-benzene to yield the (3S,4R,5R)-3-[(4S)-2,2-dimethyl-[1,3]dioxolan-4-ylmethoxy]-5-hydroxy-4-[4-[3-(2-nitro-phenoxy)-propoxy]-phenyl]-piperidine-1-carboxylic acid tert-butyl ester as colorless oil; MS: 603 (M+H)⁺.

(c) In analogy to the procedure described in example 1) (f) the (3S,4R,5R)-3-[(4S)-2,2-dimethyl-[1,3]dioxolan-4-ylmethoxy]-5-hydroxy-4-[4-[3-(2-nitro-phenoxy)-propoxy]-phenyl]-piperidine-1-carboxylic acid tert-butyl ester was reacted with 3-chloromethyl-1-methoxy-naphthalene [example 1) (α)] to yield the (3S,4R,5R)-3-[(4S)-2,2-dimethyl-[1,3]dioxolan-4-ylmethoxy]-5-(4-methoxy-naphthalen-2-ylmethoxy)-4-[4-[3-(2-nitro-phenoxy)-propoxy]-phenyl]-piperidine-1-carboxylic acid tert-butyl ester as colorless oil; MS: 773 (M+H)⁺.

(d) In analogy to the procedure described in example 1) (g) the (3S,4R,5R)-3-[(4S)-2,2-dimethyl-[1,3]dioxolan-4-ylmethoxy]-5-(4-methoxy-naphthalen-2-ylmethoxy)-4-[4-[3-(2-nitro-phenoxy)-propoxy]-phenyl]-piperidine-1-carboxylic acid tert-butyl ester was deprotected with HCl in methanol to yield the (R)-3-[(3S,4R,5R)-5-(4-methoxy-naphthalen-2-ylmethoxy)-4-[4-[3-(2-nitro-phenoxy)-propoxy]-phenyl]-piperidin-3-yloxy]-propane-1,2-diol as light yellow solid; MS: 633 (M+H)⁺.

Example 9

(R)-1-[(3S,4R,5R)-5-(4-methoxy-naphthalen-2-ylmethoxy)-4-[4-[3-(2-nitro-phenoxy)-propoxy]-phenyl]-piperidin-3-yloxy]-3-[1,2,4]triazol-1-yl-propan-2-ol (a) In analogy to the procedure described in example 1 (h) the (R)-3-[(3S,4R,5R)-5-(4-methoxy-naphthalen-2-ylmethoxy)-4-[4-[3-(2-nitro-phenoxy)-propoxy]-phenyl]- piperidin-3-yloxy]-propane-1,2-diol was treated with di-tert.-butyldicarbonate to yield the (3S,4R,5R)-3-[(2R)-2,3-dihydroxy-propoxy]-5-(4-methoxy-naphthalen-2-ylmethoxy)-4-[4-[3-(2-nitro-phenoxy)-propoxy]-phenyl]-piperidine-1-carboxylic acid tert-butyl ester as light yellow foam; MS: 733 (M+H)$^+$.

(b) In analogy to the procedure described in example 1 (i) (3S,4R,5R)-3-[(2R)-2,3-dihydroxy-propoxy]-5-(4-methoxy-naphthalen-2-ylmethoxy)-4-[4-[3-(2-nitro-phenoxy)-propoxy]-phenyl]-piperidine-1-carboxylic acid tert-butyl ester was treated with toluol-4-sulfochlorid to yield the (3S,4R,5R)-3-[(2S)-2-hydroxy-3-(toluene-4-sulfonyloxy)-propoxy]-5-(4-methoxy-naphthalen-2-ylmethoxy)-4-[4-[3-(2-nitro-phenoxy)-propoxy]-phenyl]-piperidine-1-carboxylic acid tert-butyl ester as light yellow foam; MS: 887 (M)$^+$.

(c) In analogy to the procedure described in example 1) (j) the (3S,4R,5R)-3-[(2S)-2-hydroxy-3-(toluene-4-sulfonyloxy)-propoxy]-5-(4-methoxy-naphthalen-2-ylmethoxy)-4-[4-[3-(2-nitro-phenoxy)-propoxy]-phenyl]-piperidine-1-carboxylic acid tert-butyl ester was treated with sodium hydroxide solution in dimethylsulfoxide to yield the (3R,4R,5S)-3-(4-methoxy-naphthalen-2-ylmethoxy)-4-[4-[3-(2-nitro-phenoxy)-propoxy]-phenyl]-5-[(2R)-oxiranylmethoxy]-piperidine-1-carboxylic acid tert-butyl ester as light yellow foam; MS: 715 (M+H)$^+$.

(d) In analogy to the procedure described in example 1) (k) the (3R,4R,5S)-3-(4-methoxy-naphthalen-2-ylmethoxy)-4-[4-[3-(2-nitro-phenoxy)-propoxy]-phenyl]-5-[(2R)-oxiranylmethoxy]-piperidine-1-carboxylic acid tert-butyl ester was treated with [1,2,4]triazol and sodium hydride in N,N-dimethylformamide to yield the (3S,4R,5R)-3-[(2R)-2-hydroxy-3-[1,2,4]triazol-1-yl-propoxy]-5-(4-methoxy-naphthalen-2-ylmethoxy)-4-[4-[3-(2-nitro-phenoxy)-propoxy]-phenyl]-piperidine-1-carboxylic acid tert-butyl ester as colorless oil; MS: 784 (M+H)$^+$.

(e) In analogy to the procedure described in example 1) (l) the (3S,4R,5R)-3-[(2R)-2-hydroxy-3-[1,2,4]triazol-1-yl-propoxy]-5-(4-methoxy-naphthalen-2-ylmethoxy)-4-[4-[3-(2-nitro-phenoxy)-propoxy]-phenyl]-piperidine-1-carboxylic acid tert-butyl ester was deprotected with HCl in methanol to yield the (R)-1-[(3S,4R,5R)-5-(4-methoxy-naphthalen-2-ylmethoxy)-4-[4-[3-(2-nitro-phenoxy)-propoxy]-phenyl]-piperidin-3-yloxy]-3-[1,2,4]triazol-1-yl-propan-2-ol as colorless oil; MS: 684 (M+H)$^+$.

Example 10

(R)-1-imidazol-1-yl-3-[(3S,4R,5R)-5-(4-methoxy-naphthalen-2-ylmethoxy)-4-[4-[3-(2-nitro-phenoxy)-propoxy]-phenyl]-piperidin-3-yloxy]-propan-2-ol (a) In analogy to the procedure described in example 1) (k) the (3R,4R,5S)-3-(4-methoxy-naphthalen-2-ylmethoxy)-4-[4-[3-(2-nitro-phenoxy)-propoxy]-phenyl]-5-[2R)-oxiranylmethoxy]-piperidine-1-carboxylic acid tert-butyl ester was treated with imidazol and sodium hydride in N,N-dimethylformamide to yield the (3S,4R,5R)-3-[(2R)-2-hydroxy-3-imidazol-1-yl-propoxy]-5-(4-methoxy-naphthalen-2-ylmethoxy)-4-[4-[3-(2-nitro-phenoxy)-propoxy]-phenyl]-piperidine-1-carboxylic acid tert-butyl ester as colorless oil; MS: 783 (M+H)$^+$.

(b) In analogy to the procedure described in example 1) (l) the (3S,4R,5R)-3-[(2R)-2-hydroxy-3-imidazol-1-yl-propoxy)-5-(4-methoxy-naphthalen-2-ylmethoxy)-4-[4-[3-(2-nitro-phenoxy)-propoxy]-phenyl]-piperidine-1-carboxylic acid tert-butyl ester was deprotected with HCl in methanol to yield the (R)-1-imidazol-1-yl-3-[(3S,4R,5R)-5-(4-methoxy-naphthalen-2-ylmethoxy)-4-[4-[3-(2-nitro-phenoxy)-propoxy]-phenyl]-piperidin-3-yloxy]-propan-2-ol as colorless foam; MS: 683 (M+H)$^+$.

Example 11

(R)-3-[(3S,4R,5R)-4-[4-[3-(5-fluoro-2-methoxy-benzyloxy)-propoxy]-phenyl]-5-(4-methoxy-naphthalen-2-ylmethoxy]-piperidin-3-yloxy]-propane-1,2-diol (a) In analogy to the procedure described in example 1) (e) the (3S,4R,5R)-3-[(4S)-(2,2-dimethyl-[1,3]dioxolan-4-ylmethoxy]-5-hydroxy-4-(4-hydroxy-phenyl)-piperidine-1-carboxylic acid tert-butyl ester was treated with allyl bromide in N,N-dimethylformamide in the presence of potassium carbonate to yield the (3S,4R,5R)-4-(4-allyloxy-phenyl)-3-[(4S)-2,2-dimethyl-[1,3]dioxolan-4-ylmethoxy]-5-hydroxy-piperidine-1-carboxylic acid tert-butyl ester as colorless oil; MS: 464 (M+H)$^+$.

(b) In analogy to the procedure described in example 1) (f) the (3S,4R,5R)-4-(4-allyloxy-phenyl)-3-[(4S)-2,2-dimethyl-[1,3]dioxolan-4-ylmethoxy]-5-hydroxy-piperidine-1-carboxylic acid tert-butyl ester was reacted with 3-chloromethyl-1-methoxy-naphthalene [example 1) (α)] to yield the (3S,4R,5R)-4-(4-allyloxy-phenyl)-3-[(S)-2,2-dimethyl-[1,3]dioxolan-4-ylmethoxy]-5-(4-methoxy-naphthalen-2-ylmethoxy)-piperidine-1-carboxylic acid tert-butyl ester as colorless oil; MS: 634(M+H)$^+$.

(c) 0.40 g (0.63 mmol) of (3S,4R,5R)-4-(4-allyloxy-phenyl)-3-[(S)-2,2-dimethyl -[1,3]dioxolan-4-ylmethoxy]-5-(4-methoxy-naphthalen-2-ylmethoxy)-piperidine-1-carboxylic acid tert-butyl ester, 1.4 mg (0.0063 mmol) of palladium-II-acetate and 3.3 mg (0.0126 mmol) of triphenylphosphin were dissolved in 2 ml of tetrahydrofuran. After cooling to 5° C., 21.7 mg (0.947 mmol) of lithiumborohydride were added and the reaction mixture stirred for 4 hours without cooling. Thereafter, the reaction mixture was again cooled to 5° C. and treated with 0.32 ml of acetone, then diluted with 5 ml of saturated sodium hydrogen carbonate solution and extracted twice with 5 ml of ether. The combined organic phases were washed once with a small amount of water, dried over magnesium sulphate, evaporated under reduced pressure and dried in a high vacuum. The thus-obtained crude product was separated on silica gel using a mixture of dichloromethane/ethyl acetate (4/1) as the eluent and yielded 0.343 g (0.578 mmol), 91.5%, (3S,4R,5R)-3-[(4S)-2,2-dimethyl-[1,3]dioxolan-4-ylmethoxy]-4-(4-hydroxy-phenyl)-5-(4-methoxy-naphthalen-2-ylmethoxy)-piperidine-1-carboxylic acid tert-butyl ester as colorless oil; MS: 594 (M+H)$^+$.

(d) In analogy to the procedure described in example 1 (e) the (3S,4R,5R)-3-[(4S)-2,2-dimethyl-[1,3]dioxolan-4-ylmethoxy]-4-(4-hydroxy-phenyl)-5-(4-methoxy-naphthalen-2-ylmethoxy)-piperidine-1-carboxylic acid tert-butyl ester was treated with the 2-(3-chloropropoxymethyl)-4-fluoro-1-methoxy-benzene [example 11 (a)]to yield the (3S,4R,5R)-3-[(4S)-2,2-dimethyl-[1,3] dioxolan-4-ylmethoxy]-4-[4-[3-(5-fluoro-2-methoxy-benzyloxy)-propoxy]-phenyl]-5-(4-methoxy-naphthalen-2-ylmethoxy)-piperidine-1-carboxylic acid tert-butyl ester as light yellow oil; MS: 790 (M+H)$^+$.

(e) In analogy to the procedure described in example 1) (g) the (3S,4R,5R)-3-[(4S) 2,2-dimethyl-[1,3]dioxolan-4-ylmethoxy]-4-[4-[3-(5-fluoro-2-methoxy-benzyloxy)-propoxy]-phenyl]-5-(4-methoxy-naphthalen-2-ylmethoxy)-piperidine-1-carboxylic acid tert-butyl ester was deprotected with HCl in methanol to yield the (R)-3-[(3S,4R, 5R)-4-[4-[3-(5-fluoro-2-methoxy-benzyloxy)-propoxy]-phenyl]-5-(4-methoxy-naphthalen-2-ylmethoxy]-piperidin-3-yloxy]-propane-1,2-diol as amorphous solid; MS: 650 (M+H)$^+$.

Preparation of 2-(3-chloro-propoxymethyl)-4-fluoro-1-methoxy-benzene (a) 0.870 g (5.00 mmol) of 2-chloromethyl-4-fluoro-1-methoxy-benzene [B. Maziere, N. Dat-Xuong, Chim. Ther. (3), 1–9(1968)]and 0.83 ml of 3-chloro-1-propanol were dissolved in 4.8 ml of N,N-dimethylformamide. 0.267 g (6.23 mmol) of sodium hydride (55% dispersion in mineral oil) was added in small portions over 2 hours keeping the temperature at 10–15° C. After 1 hour stirring at room temperature, 0.032 g (0.75 mmol) of sodium hydride dispersion was added and the mixture stirred another 3 hours. Thereupon, the reaction mixture was poured into 50 ml of ice-water and extracted three times with 100 ml of ether. The combined ether phases were subsequently washed with water, dried over magnesium sulphate and evaporated on a rotary evaporator at a maximum 40° C. The residue (1.5 g) which was thereby obtained was chromatographed on silica gel with dichloromethane/hexane (1:1). There was thus obtained 0.928 g (3.99 mmol), 80%,2-(3-chloro-propoxymethyl)-4-fluoro-1-methoxy-benzene as a colorless oil: MS: 232, 234 (M)$^+$.

Example 12

(R)-3-[(3S,4R,5R)-4-[4-[3-(2-chloro-phenoxy)-propoxy]-phenyl]-5-(4-methoxy-naphthalen-2-ylmethoxy)-piperidin-3-yloxy]-propane-1,2-diol (a) In analogy to the procedure described in example 1) (e) the (3S,4R,5R)-3-[(4S) (2,2-dimethyl-[1,3]dioxolan-4-ylmethoxy]-5-hydroxy-4-(4-hydroxy-phenyl)-piperidine-1-carboxylic acid tert-butyl ester was treated with the 1-(3-brom-propoxy)-2-chlor-benzol (WO 97/09311) to yield the (3S,4R,5R)-4-[4-[3-(2-chloro-phenoxy)-propoxy]-phenyl]-3-[(4S)-2,2-dimethyl-[1,3]dioxolan-4-ylmethoxy]-5-hydroxy-piperidine-1-carboxylic acid tert-butyl ester as colorless oil; MS: 592.3 (M+H)$^+$.

(b) In analogy to the procedure described in example 1) (f) the (3S,4R,5R)-4-[4-[3-(2-chloro-phenoxy)-propoxy]-phenyl]-3-[(4S)-2,2-dimethyl-[1,3]dioxolan-4-ylmethoxy]-5-hydroxy-piperidine-1-carboxylic acid tert-butyl ester was reacted with the 3-chloromethyl-1-methoxy-naphthalene [example 1) (α)] to yield the (3S,4R,5R)-4-[4-[3-(2-chloro-phenoxy)-propoxy]-phenyl]-3-[(4S)-2,2-dimethyl-[1,3] dioxolan-4-ylmethoxy]-5-(4-methoxy-naphthalen-2-ylmethoxy)-piperidine-1-carboxylic acid tert-butyl ester as colorless oil; MS: 762.3 (M+H)$^+$.

(c) In analogy to the procedure described in example 1 (g) the (3S,4R,5R)-4-[4-[3-(2-chloro-phenoxy)-propoxy]-phenyl]-3-[(4S)-2,2-dimethyl-[1,3]dioxolan-4-ylmethoxy]-5-(4-methoxy-naphthalen-2-ylmethoxy)-piperidine-1-carboxylic acid tert-butyl ester was deprotected with HCl in methanol to yield the (R)-3-[(3S,4R,5R)-4-[4-[3-(2-chloro-phenoxy)-propoxy]-phenyl]-5-(4-methoxy-naphthalen-2-ylmethoxy)-piperidin-3-yloxy]-propane-1,2-diol as colorless oil; MS: 622.2 (M+H)$^+$.

Example 13

(R)-3-[(3S,4R,5R)-4-[4-[3-(2-Methoxy-benzyloxy)-propoxy]-phenyl]-5-(4methoxy-naphthalen-2-ylmethoxy)-piperidin-3-ylmethoxy]-propane-1,2-diol (a) To a hot solution of 40.2 g (70.6 mmol) of (3RS,4RS, 5SR)-1-benzyl-4-(4-methoxy-phenyl)-5-trityloxymethyl-piperidin-3-ol [WO 9709311, Example 148 (c)]in 600 ml of ethyl acetate and 200 ml of methanol, 6.4 g (42.3 mmol) of L(+)-mandelic acid, dissolved in 20 ml of methanol, were added and the mixture heated to reflux. The solvent was distilled off until the first solid material appeared. Then, under stirring the solution was cooled to room temperature. The solid formed was filtered and dried under vacuum. After two crystallizations 17.2 g of (3R,4R,5S)-1-benzyl-4-(4-methoxy-phenyl)-5-trityloxymethyl-piperidin-3-ol (S)-hydroxy-phenyl-acetate were obtained as colorless crystals; e.e.>99.5% (The optical purity was determined by gas chromatography after hydrogenolysis with palladium-on-charcoal in methanol and treatment with hydrogenchloride in methanol to obtain the unprotected derivative which was then trifluoroacetylated).

(b) 33.3 (46.13 mmol) of (3R,4R,5S)-1-benzyl-4-(4-methoxy-phenyl)-5-trityloxymethyl-piperidin-3-ol (S)-hydroxy-phenyl-acetate were treated with a cold aqueous solution of 7.3 g (69.2 mmol) of sodium carbonate in 100 ml water and 600 ml of ethyl acetate. The aqueous phase was separated and extracted twice with 200 ml of ethyl acetate. The combined organic phases were dried over sodium sulfate and evaporated under reduced pressure to yield 25 g of (3R,4R,5S)-1-benzyl-4-(4-methoxy-phenyl)-5-trityloxymethyl-piperidin-3-ol as a colorless oil which was directly used without further purification.

The crude base was dissolved in 800 ml of dichloromethane and cooled to −78° C. Thereupon, 131.5 ml (131.5 mmol) of borotribromide (1 M in dichloromethane) were added dropwise under stirring so that the temperature was kept at about −65° C. After complete addition, the reaction mixture was left to warm up during the night. To complete the reaction another 43.8 ml (43.83 mmol) of borotribromide were added under the aforementioned conditions, and after additional 7 hours of stirring at room temperature the reaction was complete. Then the reaction mixture was cooled to 0° C. and the precipitated product was isolated by filtration. The mother liquor was concentrated to half of its volume and cooled to 0° C. and a second crop of solid product was obtained. The combined fractions were dried under high vacuum during 15 hours at room temperature to give 18.8 g of (3R,4R,5S)-1-benzyl-5-hydroxymethyl-4-(4-hydroxy-phenyl)-piperidin-3-ol hydrobromide [MS: 314 (M+H)⁺] as a yellowish solid. The crude product was used in the next step without further purification.

(c) The solution of 18.6 g (47.2 mmol) of crude (3R,4R,5S)-1-benzyl-5-hydroxymethyl-4-(4-hydroxy-phenyl)-piperidin-3-ol hydrobromide in 250 ml of methanol was flushed with argon, treated with 1.5 g of palladium-on-charcoal (10%) and exhaustively hydrogenated at room temperature under normal pressure during 18 hours. The reaction mixture was filtered over Dicalit and the residue washed twice with 100 ml of warm methanol. The methanol solutions were combined and evaporated under reduced pressure to yield 12.79 g of (3R,4R,5S)-5-hydroxymethyl-4-(4-hydroxy-phenyl)-piperidin-3-ol hydrobromide [MS: 223 (M)⁺] as a yellowish foam which was used in the next step without further purification.

(d) 12.79 g (42.05 mmol) of the crude (3R,4R,5S)-5-hydroxymethyl-4-(4-hydroxy-phenyl)-piperidin-3-ol hydrobromide and 7.1 g (84.1 mmol) of hydrogencarbonate were dispersed in 60 ml of water and 60 ml of dioxane. A solution of 9.6 g (44.1 mmol) of di-tert-butyl-dicarbonate in 60 ml of dioxane was added dropwise at room temperature. After complete addition stirring was continued for 18 hours at room temperature. Then the reaction mixture was diluted with 300 ml of water and extracted with 300 ml of ethyl acetate. The aqueous phase was separated and extracted twice with 150 ml of ethyl acetate. The combined organic phases were dried over sodium sulfate and evaporated under reduced pressure. The residue which was thereby obtained was chromatographed on silica gel with a 95:5 mixture of dichloromethane and methanol. There where thus obtained 11.2 g of (3R,4R,5S)-3-hydroxy-5-hydroxymethyl-4-(4-hydroxy-phenyl)-piperidine-1-carboxylic acid tert-butyl ester in the form of a yellowish foam; MS: 324 (M+H)⁺.

(e) 11.2 g (34.63 mmol) of (3R,4R,5S)-3-hydroxy-5-hydroxymethyl-4-(4-hydroxy-phenyl)-piperidine-1-carboxylic acid tert-butyl ester were stirred together with 7.7 g (55.41 mmol) of potassium carbonate and 8.9 g (1.2 moleq) of 1-(3-chloro-propoxymethyl)-2-methoxy-benzene in N,N-dimethylformamide at 100–110° C. during 18 hours. To complete the reaction another 1.5 g (0.2 moleq) of 1-(3-chloro-propoxymethyl)-2-methoxy-benzene were added and the mixture was stirred at 100–110° C. during additional 12 hours. Thereupon the reaction mixture was cooled to room temperature, then diluted with 540 ml of water and 400 ml of dichloromethane. The aqueous phase was separated and extracted twice with 250 ml of dichloromethane. The combined organic phases were dried over sodium sulfate and evaporated under reduced pressure. The residue which was thereby obtained was chromatographed on silica gel with a 98:2 mixture of dichloromethane and methanol as the eluent. There where thus obtained 16.2 g of (3R,4R,5S)-3-hydroxy-5-hydroxymethyl-4-[4-[3-(2-methoxy-benzyloxy)-propoxy]-phenyl]-piperidine-1-carboxylic acid tert-butyl ester in the form of a yellowish foam; MS: 524 (M+Na)⁺.

(f) To a solution of 16.1 g (32.1 mmol) of (3R,4R,5S)-3-hydroxy-5-hydroxymethyl-4-[4-[3-(2-methoxy-benzyloxy)-propoxy]-phenyl]-piperidine-1-carboxylic acid tert-butyl ester in 80 ml of pyridine, 11 g (38.5 mmol) of triphenyl-chloromethane and 0.04 g (0.31 mmol) of 4-dimethylaminpyridine were added. The solution was stirred at room temperature for 60 hours. For the working-up the reaction mixture was evaporated under reduced pressure and the residue which was thereby obtained was dissolved in 900 ml of dichloromethane. The organic phase was washed with 250 ml of water, then dried over sodium sulfate and evaporated under reduced pressure. The crude material was chromatographed on silica gel with a 98:2 mixture of dichloromethane and methanol as the eluent. There were thus obtained 16.3 g of (3R,4R,5S)-3-hydroxy-4-[4-[3-(2-methoxy-benzyloxy)-propoxy]-phenyl]-5-trityloxymethyl-piperidine-1-carboxylic acid tert-butyl ester in the form of an colorless oil; MS: 766 (M+Na)⁺.

(g) Under an argon atmosphere 16.2 g (21.7 mmol) of (3R,4R,5S)-3-hydroxy-4-[4-[3-(2-methoxy-benzyloxy)-propoxy]-phenyl]-5-trityloxymethyl-piperidine-1-carboxylic acid tert-butyl ester and 5.8 g (28.3 mmol) of 3-chloromethyl-1-methoxy-naphthalen [WO 9709311] were dissolved in 150 ml of N,N-dimethylformamide, treated at 0° C. with 1.7 g (about 34.8 mmol) of sodium hydride dispersion in refined oil (55–65%), and the reaction mixture was warmed to room and stirred for 15 hours. Thereupon the N,N-dimethylformamide was evaporated under reduced pressure and the residue which was thereby obtained was hydrolyzed by 200 ml of ice-water and extracted with 500 ml of dichloromethane. The aqueous phase was separated and extracted twice with 200 ml of dichloromethane. The combined organic phases were dried over sodium sulfate and evaporated under reduced pressure. The residue which was thereby obtained was chromatographed on silica gel with dichloromethane. There where thus obtained 18.4 g of (3R,4R,5S)-4-[4-[3-(2-methoxy-benzyloxy)-propoxy]-phenyl]-3-(4-methoxy-naphthalen-2-ylmethoxy)-5-trityloxymethyl-piperidine-1-carboxylic acid tert-butyl ester in the form of a yellowish oil; MS: 937 (M+Na)⁺.

(h) To the solution of 18.3 g (20.1 mmol) of (3R,4R,5S)-4-[4-[3-(2-methoxy-benzyloxy)-propoxy]-phenyl]-3-(4-methoxy-naphthalen-2-ylmethoxy)-5-trityloxymethyl-piperidine-1-carboxylic acid tert-butyl ester in 200 ml of dichloromethane was poured under stirring at room temperature a solution of 9.4 g (80.4 mmol) of trifluoroacetic acid and 17.2 g (80.4 mmol) of trifluoroacetic acid anhydride in 20 ml of dichloromethane. After 30–40 seconds the reaction flask was placed in a dry ice/acetone mixture and simultanously 61.3 g (603.3 mmol) of triethylamine were added, and stirring was continued at 0° C. for 5 minutes. Then 80 ml of methanol were added and stirring was continued for 15 minutes. Thereupon the reaction mixture was treated with 200 ml of a saturated solution of sodium hydrogencarbonate and 500 ml of dichloromethane. The aqueous phase was separated and extracted two times with 150 ml of dichloromethane. The combined organic phases were dried over sodium sulfate and evaporated under reduced pressure to yield 19 g of the crude alcohol. The residue which was thereby obtained was chromatographed on silica gel with a 98:2 mixture of dichloromethane and methanol as the eluent. There where thus obtained 12.9 g of (3S,4R,5R)-3-hydroxymethyl-4-[4-[3-(2-methoxy-benzyloxy)-propoxy]-phenyl]-5-(4-methoxy-naphthalen-2-ylmethoxy)-piperidine-1-carboxylic acid tert-butyl ester in the form of a yellowish oil; MS: 694 (M+Na)⁺.

(i) To the solution of 2.0 g of (3S,4R,5R)-3-hydroxymethyl-4-[4-[3-(2-methoxy-benzyloxy)-propoxy]-phenyl]-5-(4-methoxy-naphthalen-2-ylmethoxy)-piperidine-1-carboxylic acid tert-butyl ester in 50 ml of N,N-dimethylformamide were added 1.1 g (about 23.8 mmol) of sodium hydride dispersion in refined oil (55–65%), and the reaction mixture was heated to 50° C. under argon for 1 hour. Then, 6.8 g (23.8 mmol) of (R)-(–)-2,2-dimethyl 4-(hydroxymethyl)-1,3-dioxolane-p-toluene sulfonate were added and stirring was continued at 50° C. for another 3 hours. Subsequently, the reaction mixture was evaporated under reduced pressure and the residue which was obtained was hydrolyzed with 50 ml of ice-water and extracted with 100 ml of dichloromethane. The aqueous phase was separated and extracted twice with 50 ml of dichloromethane. The combined organic phases were dried over sodium sulfate and then evaporated under reduced pressure. The residue which was thereby obtained was chromatographed on silica gel with a 99:1 mixture of dichloromethane and methanol as the eluent. There where thus obtained 1.3 g of (3S,4R,5R)-3-[(S)-2,2-dimethyl-[1,3]dioxolan-4-ylmethoxymethyl]-4-[4-[3-(2-methoxy-benzyloxy)-propoxy]-phenyl]-5-(4-methoxy-naphthalen-2-ylmethoxy)-piperidine-1-carboxylic acid tert-butyl ester in the form of a yellowish oil; MS: 803 $(M+NH_4)^+$.

(j) A solution of 4.7 g (6 mmol) of (3S,4R,5R)-3-[(S)-2,2-dimethyl-[1,3]dioxolan-4-ylmethoxymethyl]-4-[4-[3-(2-methoxy-benzyloxy)-propoxy]-phenyl]-5-(4-methoxy-naphthalen-2-ylmethoxy)-piperidine-1-carboxylic acid tert-butyl ester in 50 ml of methanol and 44.4 ml of 2.7M hydrogenchloride in methanol was stirred at room temperature for 1 hour. Subsequently, the reaction mixture was cooled to 0° C. and 20.1 g (239 mmol) of solid sodium hydrogencarbonate were added. Stirring was continued as long as carbondioxide was formed and the reaction mixture had reached room temperature. Then the mixture was adjusted to pH 8–9 by addition of 2 N sodium hydroxide solution and diluted with 250 ml of dichloromethane. The aqueous phase was separated and the organic phase dried over sodium sulfate and finally evaporated under reduced pressure. The residue which was thereby obtained was chromatographed on silica gel with a 90:10:0.1 mixture of dichloromethane, methanol and ammonium hydroxide as the eluent. There where thus obtained 2.7 g of (R)-3-[(3S,4R,5R)-4-[4-[3-(2-methoxy-benzyloxy)-propoxy]-phenyl]-5-(4-methoxy-naphthalen-2-ylmethoxy)-piperidin-3-ylmethoxy]-propane-1,2-diol in the form of an amorphous solid MS: 646 $(M+H)^+$.

Example 14

(3S,4R,5R)-[4-[4-[3-(2-Methoxy-benzyloxy)-propoxy]-phenyl]-5-(4-methoxy-naphthalen-2-ylmethoxy)-piperidin-3-yl]-methanol In an analogous manner to that described in Example 13 (j) by cleavage of the BOC group using a solution of hydrogen chloride in methanol, starting from (3S,4R,5R)-3-hydroxymethyl-4-[4-[3-(2-methoxy-benzyloxy)-propoxy]-phenyl]-5-(4-methoxy-naphthalen-2-ylmethoxy)-piperidine-1-carboxylic acid tert-butyl ester [Example 13 (h)] there was obtained (3S,4R,5R)-[4-[4-[3-(2-methoxy-benzyloxy)-propoxy]-phenyl]-5-(4-methoxy-naphthalen-2-ylmethoxy)-piperidin-3-yl]-methanol as a colorless foam; MS: 572 $(M+H)^+$.

Example 15

(3S,4R,5R)-3-Imidazol-1-ylmethyl-4-[4-[3-(2-methoxy-benzyloxy)-propoxy]-phenyl]-5-(4-methoxy-naphthalen-2-ylmethoxy)-piperidine dihydrochloride (a) To a solution of 1.5 g (2.2 mmol) of (3S,4R,5R)-3-hydroxymethyl-4-[4-[3-(2-methoxy-benzyloxy)-propoxy]-phenyl]-5-(4-methoxy-naphthalen-2-ylmethoxy)-piperidine-1-carboxylic acid tert-butyl ester [Example 13 (h)] in 40 ml of tetrahydrofurane were added 0.9 ml (6.7 mmol) of triethylamine and thereafter dropwise at 0° C. 512 mg (4.5 mmol) of methanesulphonyl chloride. The reaction solution was stirred at room temperature for 2 hours. For the working-up, the reaction solution was diluted with 50 ml of dichloromethane, extracted with 20 ml of saturated sodium hydrogencarbonate solution, dried over sodium sulfate and evaporated under reduced pressure. The solid crude mesylate was dissolved in 30 ml of N,N-dimethylformamide and thereafter added dropwise to a solution beforehand prepared of 456 mg (6.7 mmol) of imidazole and 322 mg (about 6.7 mmol) of sodium hydride dispersion in refined oil (55–65%) in 10 ml of N,N-dimethylformamide. The reaction mixture was stirred at 100° C. for 6 hours and thereafter evaporated under reduced pressure. The residue was taken up in 50 ml of dichloromethane and then extracted with 20 ml of saturated sodium hydrogencarbonate solution. The organic phase was separated and dried over sodium sulfate and subsequently evaporated under reduced pressure. For purification, the crude product was chromatographed on silica gel using a 98:2 mixture of dichloromethane and methanol as the eluent. There were obtained 1.4 g of (3R,4R,5R)-3-imidazol-1-ylmethyl-4-{4-[3-(2-methoxy-benzyloxy)-propoxy]-phenyl}-5-(4-methoxy-naphthalen-2-ylmethoxy)-piperidine-1-carboxylic acid tert-butyl ester as a yellowish foam; MS: 722 $(M+H)^+$.

(b) In an analogous manner to that described in Example 13 (j) by cleavage of the BOC group using a solution of hydrogen chloride in methanol, starting from (3R,4R,5R)-3-imidazol-1-ylmethyl-4-{4-[3-(2-methoxy-benzyloxy)-propoxy]-phenyl}-5-(4-methoxy-naphthalen-2-ylmethoxy)-piperidine-1-carboxylic acid tert-butyl ester there was obtained (3S,4R,5R)-3-imidazol-1-ylmethyl-4-[4-[3-(2-methoxy-benzyloxy)-propoxy]-phenyl]-5-(4-methoxy-naphthalen-2-ylmethoxy)-piperidine dihydrochloride as an amorphous solid; MS: 622 $(M+H)^+$.

Example 16

Mixture of (RS)-and (SR)-3-[(3SR,4RS,5RS)-4-[4-(3-Benzyloxy-propoxy)-phenyl]-5-(naphthalen-2-ylmethoxy)-piperidin-3-ylmethoxy]-propane-1,2-diol (a) In an analogous manner to that described in Example 13 (g), by alkylating (3SR,4RS,5RS)-4-[4-(3-benzyloxy-propoxy)-phenyl]-3-hydroxymethyl-5-(naphthalen-2ylmethoxy)-piperidine-1-carboxylic acid tert-butyl ester [WO 9709311, Example 148 (h)] with allylbromide there was obtained (3SR,4RS,5RS)-3-allyloxymethyl-4-[4-(3-benzyloxy-propoxy)-phenyl]-5-(naphthalen-2-ylmethoxy)-piperidine-1-carboxylic acid tert-butyl ester as a colorless solid; MS: 652 (M+H)$^+$.

(b) A solution of 91 mg (0.3 mmol) of potassium peroxodisulfate, 3.0 mg (0.009 mmol) of potassium ferrocyanide, 1.1 mg (0.003 mmol) of potassium osmate dihydrate and 84 mg (0.6 mmol) of potassium carbonate in 1 ml of water was stirred at room temperature for 20 minutes and thereafter cooled to 0° C. Thereto were added 7.2 mg (0.07 mmol) of methanesulfonamide and a solution of 198 mg (0.3 mmol) of (3SR,4RS,5RS)-3-allyloxymethyl-4-[4-(3-benzyloxy-propoxy)-phenyl]-5-(naphthalen-2-ylmethoxy)-piperidine-1-carboxylic acid tert-butyl ester in 2 ml of tert-butanol. After the complete addition, stirring was continued at room temperature for 48 hours. The mixture was diluted with 5 ml of sodium sulfite solution (0.2 N) and 2 ml of water and extracted 3 times with 10 ml of dichloromethane each time. The combined organic phases were washed with 10 ml of saturated sodium hydrogencarbonate solution, then dried over sodium sulfate and evaporated under reduced pressure. The thus obtained crude product was chromatographed on silica gel with a 98:2 mixture of dichloromethane and methanol as the eluent. There were thus obtained 153 mg of a mixture of (3RS,4SR,5SR)- and (3SR,4RS,5RS)-4-[4-(3-benzyloxy-propoxy phenyl]-3-[(2RS)-2,3-dihydroxy-propoxymethyl)]-5-(naphthalen-2-ylmethoxy)-piperidine-1-carboxylic acid tert-butyl ester as a yellowish oil; MS: 686 (M+H)$^+$.

(c) In an analogous manner to that described in Example 13 (j) by cleavage of the BOC group using a solution of hydrogen chloride in methanol, starting from of a mixture of (3RS,4SR,5SR)- and (3SR,4RS,5RS)-4-[4-(3-benzyloxy-propoxy)-phenyl]-3-[(2RS)-2,3-dihydroxy-propoxymethyl)]-5-(naphthalen-2-ylmethoxy)-piperidine-1-carboxylic acid tert-butyl ester there was obtained a mixture of (RS)- and (SR)-3-[(3SR,4RS,5RS)-4-[4-(3-benzyloxy-propoxy)-phenyl]-5-(naphthalen-2-ylmethoxy)-piperidin-3-ylmethoxy]-propane-1,2-diol-as an amorphous colorless solid; MS: 586 (M+H)$^+$.

Example 17

Mixture of (RS)- and (SR)-3-[(3SR,4RS,5RS)-4-[4-[3-(2-methoxy-benzyloxy)-propoxy]-phenyl]-5-(naphthalen-2-ylmethoxy)-piperidin-3-ylmethoxy]-propane-1,2-diol (a) In an analogous manner to that described in Example 13 (e), by alkylating (3RS,4RS,5SR)-3-hydroxy-5-hydroxymethyl-4-(4-hydroxy-phenyl)-piperidin-1-carbonsäure tert-butylester [WO 9709311, Example 148 (f)] with 1-(3-chloro-propoxymethyl)-2-methoxy-benzene [WO 9709311] there was obtained (3RS,4RS,5SR)-3-hydroxy-5-hydroxymethyl-4-[4-[3-(2-methoxy-benzyloxy)-propoxy]-phenyl]-piperidine-1-carboxylic acid tert-butyl ester as an amorphous colorless solid; MS: 519 (M+NH$_4$)$^+$.

(b) In an analogous manner to that described in Example 13 (f), by reacting (3RS,4RS,5SR)-3-hydroxy-5-hydroxymethyl-4-[4-[3-(2-methoxy-benzyloxy)-propoxy]-phenyl]-piperidine-1-carboxylic acid tert-butyl ester with triphenylchloromethane there was obtained (3RS,4RS,5SR)-3-hydroxy-4-[4-[3-(2-methoxy-benzyloxy)-propoxy]-phenyl]-5-trityloxymethyl-piperidine-1-carboxylic acid tert-butyl ester as a colorless foam; MS: 761 (M+NH$_4$)$^+$.

(c) In an analogous manner to that described in Example 13 (g), by alkylating (3RS,4RS,5SR)-3-hydroxy-4-[4-[3-(2-methoxy-benzyloxy)-propoxy]-phenyl]-5-trityloxymethyl-piperidine-1-carboxylic acid tert-butyl ester with 2-bromo-methylnaphthalene there was obtained (3RS,4RS,5SR)-4-[4-[3-(2-methoxy-benzyloxy)-propoxy]-phenyl]-3-(naphthalen-2-ylmethoxy)-5-trityloxymethyl-piperidine-1-carboxylic acid tert-butyl ester as a colorless oil; MS: 907 (M+Na)$^+$.

(d) In an analogous manner to that described in Example 13 (h), by deprotecting (3RS,4RS,5SR)-4-[4-[3-(2-methoxy-benzyloxy)-propoxy]-phenyl]-3-(naphthalen-2-ylmethoxy)-5-trityloxymethyl-piperidine-1-carboxylic acid tert-butyl there was obtained (3SR,4RS,5RS)-3-hydroxymethyl-4-[4-[3-(2-methoxy-benzyloxy)-propoxy]-phenyl]-5-(naphthalen-2-ylmethoxy)-piperidine-1-carboxylic acid tert-butyl ester as a yellowish foam; MS: 642 (M+H)$^+$.

(e) In an analogous manner to that described in Example 13 (g), by alkylating (3SR,4RS,5RS)-3-hydroxymethyl-4-[4-[3-(2-methoxy-benzyloxy)-propoxy]-phenyl]-5-(naphthalen-2-ylmethoxy)-piperidine-1-carboxylic acid tert-butyl ester with allylbromide there was obtained (3SR,4RS,5RS)-3-allyloxymethyl-4-[4-[3-(2-methoxy-benzyloxy)-propoxy]-phenyl]-5-(naphthalen-2-ylmethoxy)-piperidine-1-carboxylic acid tert-butyl ester as a colorless oil; MS: 682 (M+H)$^+$.

(f) In an analogous manner to that described in Example 16 (b), by hydroxylating (3SR,4RS,5RS)-3-allyloxymethyl-4-[4-[3-(2-methoxy-benzyloxy)-propoxy]-phenyl]-5-(naphthalen-2-ylmethoxy)-piperidine-1-carboxylic acid tert-butyl ester there was obtained a mixture of (3SR,4RS,5RS)- and (3RS,4SR,5SR)-3-[(2RS)-2,3-dihydroxy-propoxymethyl]-4-[4-[3-(2-methoxy-benzyloxy)-propoxy]-phenyl]-5-(naphthalen-2-ylmethoxy)-piperidine-1-carboxylic acid tert-butyl ester as a colorless oil; MS: 733 (M+NH$_4$)$^+$.

(g) A solution of 63 mg (0.08 mmol) of a mixture of (3SR,4RS,5RS)- and (3RS,4SR,5SR)-3-[(2RS)-2,3-dihydroxy-propoxymethyl]-4-[4-[3-(2-methoxy-benzyloxy)-propoxy]-phenyl]-5-(naphthalen-2-ylmethoxy)-piperidine-1-carboxylic acid tert-butyl ester in 5 ml of dry dichloromethane was treated with 57.1 mg (0.25 mmol) of anhydrous zinc bromide and the mixture was stirred at room temperature for 5 hours. Subsequently, the solvent was distilled off under reduced pressure, the residue was taken up in 10 ml of dichloromethane and treated with 4 ml of saturated sodium hydrogencarbonate solution. Thereafter the organic phase was dried over sodium sulfate and evaporated under reduced pressure. For purification, the residue was chromatographed on silica gel using a 90:10:0.1 mixture of dichloromethane, methanol and ammonium hydroxide as the eluent. There were obtained 41 mg of a mixture of (RS)- and (SR)-3-[(3SR,4RS,5RS)-4-[4-[3-(2-methoxy-benzyloxy)-propoxy]-phenyl]-5-(naphthalen-2-ylmethoxy)-piperidin-3-ylmethoxy]-propane-1,2-diol in the form of a yellowish foam; MS: 616 (M+H)$^+$.

Example 18

(R)-1-[(3S,4R,5R)-4-[4-[3-(5-fluoro-2-methoxy-benzyloxy)-propoxy]-phenyl]-5-(4-methoxy-naphthalen-2-ylmethoxy)-piperidin-3-yloxy]-3-methoxy-propan-2-ol (a) 0.500 g (0.789 mmol) of (3S,4R,5R)-4-(4-allyloxy-phenyl)-3-[(S)-2,2-dimethyl-[1,3]dioxolan-4-ylmethoxy]-5-(4-methoxy-naphthalen-2-ylmethoxy)-piperidine-1-carboxylic acid tert-butyl ester [example 11(b)] were dissolved in 7 ml of absolute methanol at 40° C., cooled to room temperature and treated with 0.16 ml of aqueous hydrochloric acid (25%). After stirring for 1 hour, the reaction mixture was neutralized with solid sodium carbonate, then evaporated. The residue obtained was redissolved in dichloromethane, filtered and evaporated on a rotary evaporator at a maximum 40° C. The crude product obtained was chromatographed on silica gel with dichloromethane/methanol (95/5). There were thus obtained 0.414 g (0.697 mmol), 88.4% (3S,4R,5R)-4-(4-allyloxy-phenyl)-3-[(2R)-2,3-dihydroxy-propoxy]-5-(4-methoxy-naphthalen-2-ylmethoxy)-piperidine-1-carboxylic acid tert-butyl ester as light yellow oil; MS: 594 (M+H)$^+$.

(b) In analogy to the procedure described in example 1 (i) the (3S,4R,5R)-4-(4-allyloxy-phenyl)-3-[(2R)-2,3-dihydroxy-propoxy)-5-(4-methoxy-naphthalen-2-ylmethoxy)-piperidine-1-carboxylic acid tert-butyl ester was treated with toluol-4-sulfochlorid to yield the (3S,4R,5R)-4-(4-allyloxy-phenyl)-3-[(2S)-2-hydroxy-3-(toluene-4-sulfonyloxy)-propoxy]-5-(4-methoxy-naphthalen-2-ylmethoxy)-piperidine-1-carboxylic acid tert-butyl ester as colorless foam; MS: 748 (M+H)$^+$.

(c) In analogy to the procedure described in example 1(j) the (3S,4R,5R)-4-(4-allyloxy-phenyl)-3-[(2S)-2-hydroxy-3-(toluene-4-sulfonyloxy)-propoxy]-5-(4-methoxy-naphthalen-2-ylmethoxy)-piperidine-1-carboxylic acid tert-butyl ester was treated with sodium hydroxide in dimethylsulfoxid to yield the (3R,4R,5S)-4-(4-allyloxy-phenyl)-3-(4-methoxy-naphthalen-2-ylmethoxy)-5-[(2R)-oxiranylmethoxy]-piperidine-1-carboxylic acid tert-butyl ester as colorless oil.

(d) In analogy to the procedure described in example 1 (k) the (3R,4R,5S)-4-(4-allyloxy-phenyl)-3-(4-methoxy-naphthalen-2-ylmethoxy)-5-[(2R)-oxiranylmethoxy]-piperidine-1-carboxylic acid tert-butyl ester was treated with sodium methylate in N,N-dimethylformamide to yield the (3S,4R,5R)-4-(4-allyloxy-phenyl)-3-[(2R)-2-hydroxy-3-methoxy-propoxy]-5-(4-methoxy-naphthalen-2-ylmethoxy)-piperidine-1-carboxylic acid tert-butyl ester as colorless oil; MS: 608 (M+H)$^+$.

(e) In analogy to the procedure described in example 11(c) the (3S,4R,5R)-4-(4-allyloxy-phenyl)-3-[(2R)-2-hydroxy-3-methoxy-propoxy]-5-(4-methoxy-naphthalen-2-ylmethoxy)-piperidine-1-carboxylic acid tert-butyl ester was treated with palladium-II-acetate, triphenylphosphin and lithiumborohydride in tetrahydrofuran to yield the (3S,4R,5R)-3-[(2R)-2-hydroxy-3-methoxy-propoxy]-4-(4-hydroxy-phenyl)-5-(4-methoxy-naphthalen-2-ylmethoxy)-piperidine-1-carboxylic acid tert-butyl ester as colorless oil; MS: 568 (M+H)$^+$.

(f) In analogy to the procedure described in example 1(e) the (3S,4R,5R)-3-[(2R)-2-hydroxy-3-methoxy-propoxy]-4-(4-hydroxy-phenyl)-5-(4-methoxy-naphthalen-2-ylmethoxy)-piperidine-1-carboxylic acid tert-butyl ester was treated with the 2-(3-chloro-propoxymethyl)-4-fluoro-1-methoxy-benzene [example 11(α)] to yield the (3S,4R,5R)-4-[4-[3-(5-fluoro-2-methoxy-benzyloxy)-propoxy]-phenyl]-3-[(2R)-2-hydroxy-3-methoxy-propoxy]-5-(4-methoxy-naphthalen-2-ylmethoxy)-piperidine-1-carboxylic acid tert-butyl ester as colorless oil; MS: 764 (M+H)$^+$.

(g) In analogy to the procedure described in example 1(l) the (3S,4R,5R)-4-{4-[3-(5 fluoro-2-methoxy-benzyloxy)-propoxy]-phenyl}-3-[(2R)-2-hydroxy-3-methoxy-propoxy]-5-(4-methoxy-naphthalen-2-ylmethoxy)-piperidine-1-carboxylic acid tert-butyl ester was deprotected with hydrochloric acid in methanol to yield the (R)-1-[(3S,4R,5R)-4-[4-[3-(5-fluoro-2-methoxy-benzyloxy)-propoxy]-phenyl]-5-(4-methoxy-naphthalen-2-ylmethoxy)-piperidin-3-yloxy]-3-methoxy-propan-2-ol as colorless oil; MS: 664 (M+H)$^+$.

Example 19

The following compounds were obtained in an analogous manner to that described in example 18 and example 1 respectively by alkylation of the (3S,4R,5R)-3-[(2R)-2-hydroxy-3-methoxy-propoxy]-4-(4-hydroxy-phenyl)-5-(4-methoxy-naphthalen-2-ylmethoxy)-piperidine-1-carboxylic acid tert-butyl ester followed by cleavage of the protecting group by means of hydrogen chloride in methanol:

1) by alkylation with 1-(3-chloro-propoxymethyl)-4-fluoro-2-methoxy-benzene and subsequent cleavage of the BOC group, (R)-1-[(3S,4R,5R)-4-[4-[3-(4-fluoro-2-methoxy-benzyloxy)-propoxy]-phenyl]-5-(4-methoxy-naphthalen-2-ylmethoxy)-piperidin-3-yloxy]-3-methoxy-propan-2-ol as a colorless oil; MS: 664 (M+H)$^+$;

2) by alkylation with 1-(3-chloro-propoxymethyl)-3-fluoro-2-methoxy-benzene and subsequent cleavage of the BOC group, (R)-1-[(3S,4R,5R)-4-[4-[3-(3-fluoro-2-methoxy-benzyloxy)-propoxy]-phenyl]-5-(4-methoxy-naphthalen-2-ylmethoxy)-piperidin-3-yloxy]-3-methoxy-propan-2-ol as a light yellow oil; MS: 664 (M+H)$^+$;

3) by alkylation with 1-(3-chloro-propoxymethyl)-3,5-difluoro-2-methoxy-benzene and subsequent cleavage of the BOC group, (R)-1-[(3S,4R,5R)-4-[4-[3-(3,5-difluoro-2-methoxy-benzyloxy)-propoxy]-phenyl]-5-(4-methoxy-naphthalen-2-ylmethoxy)-piperidin-3-yloxy]-3-methoxy-propan-2-ol as a colorless oil; MS: 682 (M+H)$^+$;

4) by alkylation with 1-(3-chloro-propoxymethyl)-4,5-difluoro-2-methoxy-benzene and subsequent cleavage of the BOC group, (R)-1-[(3S,4R,5R)-4-[4-[3-(4,5-difluoro-2-methoxy-benzyloxy)-propoxy]-phenyl]-5-(4-methoxy-naphthalen-2-ylmethoxy)-piperidin-3-yloxy]-3-methoxy-propan-2-ol as a light yellow oil; MS: 682 (M+H)$^+$.

The 1-(3-chloro-propoxymethyl)-benzene derivatives used as the alkylating agents were prepared as follows:
1-(3-Chloro-propoxymethyl)-4-fluoro-2-methoxy-benzene (a) To a solution of 1.3 g (9.3 mmol) of 4-fluoro-2-hydroxy-benzaldehyde, obtained following the method described by R. Alfred et al. in J.Chem.Soc., Perkin Trans. (1994), 1823, in 20 ml of acetone were added 0.87 ml (13.4 mmol) of methyliodide and 1.9 g (13.4 mmol) of powdered potassium carbonate. The dispersion was stirred at 45° C. for 2 hours. Subsequently, the reaction mixture was evaporated, the residue extracted with dichloromethane and water, the organic phase separated and concentrated under reduced pressure. There was obtained 1.1 g (77% of theory) of 4-fluoro-2-methoxy-benzaldehyde as a yellow solid; M: 154 (M)$^+$.

(b) An ice-cold solution of 5.6 g of 4-fluoro-2-methoxy-benzaldehyde in 75 ml of methanol was treated portionwise (5 portions within 50 minutes) with 1.51 g (40mmol) of sodium borohydride and the reaction mixture was stirred for another 1 hour at room temperature. A dispersion of 7 g of potassium hydrogencarbonate in 20 ml of water was added and the mixture stirred for 30 minutes at room temperature. Thereupon, most of the methanol was evaporated under reduced pressure and the residue extracted with dichloromethane. The organic phase was separated, dried and concentrated under reduced pressure to yield 5.15 g (91% of theory) of (4-fluoro-2-methoxy-phenyl)-methanol as a white solid; MS: 156 (M)$^+$.

(c) To a solution of 1.1 g (7 mmol) of (4-fluoro-2-methoxy-phenyl)-methanol and 0.85 g (8.4 mmol) of triethylamine in 10 ml of dichloromethane was added dropwise under an argon atmosphere at −10° C. a solution of 0.96 g (8.4 mmol) of mesylchloride in 10 ml of dichloromethane. After complete addition, the reaction mixture was stirred at room temperature for 18 hours. Thereupon, the solution was extracted two times with water and the organic phase was evaporated under reduced pressure. The residue was dissolved in 10 ml of tetrahydrofuran, treated with 2 ml of saturated aqueous sodium hydrogencarbonate solution and stirred for one hour at room temperature.

Subsequently, the mixture was extracted with dichloromethane, the organic phase separated, dried over sodium sulfate and evaporated under reduced pressure. The thus obtained crude product was chromatographed on silica gel with a 1:1 mixture of hexane and dichloromethane as the eluent. There was thus obtained 0.95 g (60% of theory) of 1-chloromethyl-4-fluoro-2-methoxy-benzene as a colorless liquid; MS: 174 (M)$^+$.

(d) To an ice-cold solution of 0.36 g (2.06 mmol) of 1-chloromethyl-4-fluoro-2-methoxy-benzene and 0.195 g (4.12 mmol) of 1-chloro-3-propanol in 3 ml of dry N,N-dimethyl-formamide were added 92.5 mg (3.09 mmol) of sodium hydride (80% dispersion in refined oil) in 3 portions at one hour intervals. After complete addition the stirring was continued for 2 hours at room temperature, then 2 ml of an saturated aqueous sodium hydrogencarbonate solution were added and the reaction mixture evaporated under reduced pressure. Subsequently, the residue was treated with a mixture of dichloromethane and water, the organic phase was separated and dried over sodium sulfate. Finally, the solvent was evaporated under reduced pressure and the crude product was purified by chromatography on silica gel with a 1:1 mixture of hexane and dichloromethane as the eluent. There were obtained 0.29 g (60% of theory) of 1-(3-chloro-propoxymethyl)-4-fluoro-2-methoxy-benzene as a colorless liquid; MS: 232 (M)$^+$.

1-(3-Chloro-propoxymethyl)-3-fluoro-2-methoxy-benzene (a) In an analogous manner to that described in (β) 3-fluoro-2-hydroxy-benzaldehyde was reduced by sodium borohydride to yield 2-fluoro-6-hydroxymethyl-phenol as a white solid; MS: 142 (M)$^+$.

(b) In an analogous manner to that described in (α) 2-fluoro-6-hydroxymethyl-phenol was alkylated with methyliodide to yield (3-fluoro-2-methoxy-phenyl)-methanol as a white solid; MS: 142 (M)$^+$.

(c) In an analogous manner to that described in (γ) (3-fluoro-2-methoxy-phenyl)-methanol was treated with mesylchloride to obtain 1-chloromethyl-3-fluoro-2-methoxy-benzene as a colorless liquid; MS: 174 (M)$^+$.

(d) In an analogous manner to that described in (δ) 1-chloromethyl-3-fluoro-2-methoxy-benzene was reacted with 1-chloro-3-propanol to yield 1-(3-chloro-propoxymethyl)-3-fluoro-2-methoxy-benzene as a colorless liquid; MS: 232 (M)$^+$.

1-(3-Chloro-propoxymethyl)-3,5-difluoro-2-methoxy-benzene (a) In an analogous manner to that described in (α) 1-(3,5-difluoro-2-hydroxy-phenyl)-ethanone was alkylated with methyliodide to yield 1-(3,5-difluoro-2-methoxy-phenyl)-ethanone as beige needles; MS: 186 (M)$^+$.

(b) The 1-(3,5-difluoro-2-methoxy-phenyl)-ethanone was transformed by an Einhorn reaction following a typical procedure given in Organikum, 18$^{th}$ ed., p.375 (Dt. Verlag der Wissenschaften) into the 3,5-difluoro-2-methoxy-benzaldehyde, which was obtained as colorless crystals; MS: 188 (M)$^+$.

(c) To an ice-cold solution of 1.7 g (9.03 mmol) of 3,5-difluoro-2-methoxy-benzaldehyde in 10 ml of dry tetrahydrofuran was added under an argon atmosphere 1 ml of borane dimethylsulfide complex. The reaction mixture was warmed up and stirred for 24 hours at room temperature. Thereupon, the mixture was again cooled to 0° C. and 5 ml of methanol were added dropwise within 30 minutes. Subsequently, the solvent was distilled and the crude product was purified by chromatography on silica gel with a 1:1 mixture of diethylether and dichloromethane as the eluent. There were obtained 0.89 g (56% of theory) of (3,5-difluoro-2-methoxy-phenyl)-methanol as a colorless liquid; MS: 174 (M)$^+$.

(d) To a mixture of 0.87 g (5.02 mmol) of of (3,5-difluoro-2-methoxy-phenyl)-methanol, 0.82 ml (7.03 mmol) of 2,6-lutidine, and 0.425 g (10 mmol) of lithium chloride in 5 ml N,N-dimethylformamide were added dropwise at 0° C. 0.5 ml (6.5 mmol) of mesylchloride. The suspension was stirred during 18 hours at room temperature and then treated with 1 ml of saturated aqueous sodium hydrogencarbonate solution. The volatile components were distilled at 35° C./1 Torr and the residue was partitioned between ethyl acetate and water. The organic phase was separated and evaporated under reduced pressure and the crude product was purified by chromatography on silica gel with dichloromethane as the eluent. There were obtained 0.49 g (51% of theory) of 1-chloromethyl-3,5-difluoro-2-methoxy-benzene as a colorless liquid; MS: 192 (M)$^+$.

(e) In an analogous manner to that described in (δ) 1-chloromethyl-3,5-difluoro-2-methoxy-benzene was reacted with 1-chloro-3-propanol to yield 1-(3-chloro-propoxymethyl)-3,5-difluoro-2-methoxy-benzene as a colorless liquid; MS: 250 (M)$^+$.

1-(3-Chloro-propoxymethyl)-4,5-difluoro-2-methoxy-benzene (a) To a suspension of 5.75 g (40 mmol) of 1,2-difluoro-4-methoxy-benzene, 2.18 g (72 mmol) of paraformaldehyde and 3.55 g (25 mmol) of phosphorouspentoxide in 20 ml of acetic acid were added dropwise 7.2 ml of aqueous hydrochloric acid (37%). Thereupon, the reaction mixture was stirred for 18 hours at room temperature and additional 4 hours at 60° C. For the working up the mixture was hydrolyzed on crushed ice and 200 ml of diethylether were added. Under vigorous stirring 50 ml of saturated aqueous sodium hydrogencarbonate solution were added dropwise, then solid sodium hydrogencarbonate was added until the evolvement of carbondioxide had ceased. Subsequently, the organic phase was separated, extracted with saturated sodium chloride solution and dried over sodium sulfate. The solvent was evaporated and the crude product distilled. There were obtained 7.1 g (92% of theory) of 1-chloromethyl-4,5-difluoro-2-methoxy-benzene as a colorless liquid; b.p. ; 92–93° C. (6 Torr) ; MS: 192 (M)$^+$.

(b) In an analogous manner to that described in (δ) 1-chloromethyl-4,5-difluoro-2-methoxy-benzene was reacted with 1-chloro-3-propanol to yield 1-(3-chloro-propoxymethyl)-4,5-difluoro-2-methoxy-benzene as a colorless liquid; MS: 250 (M)$^+$.

Example 20

The following compounds were obtained in an analogous manner to that described in example 11) (d), (e) and example 1) (e), (g) respectively by alkylation of the (3S,4R,5R)-3-[(4S)-2,2-dimethyl-[1,3]dioxolan-4-ylmethoxy]-4-(4-hydroxy-phenyl)-5-(4-methoxy-naphthalen-2-ylmethoxy)-piperidine-1-carboxylic acid tert-butyl ester with the aforementioned chlorides, followed by cleavage of the protecting groups by means of hydrogen chloride in methanol:

1) By alkylation with 1-(3-chloro-propoxymethyl)-3-fluoro-2-methoxy-benzene and subsequent cleavage of the isopropylidene and the BOC group, (R)-3-[(3S,4R,5R)-4-[4-[3-(3-fluoro-2-methoxy-benzyloxy)-propoxy]-phenyl]-5-(4-methoxy-naphthalen-2-ylmethoxy)-piperidin-3-yloxy]-propane-1,2-diol as a colorless oil; MS: 650 (M+H)$^+$;

2) by alkylation with 1-(3-chloro-propoxymethyl)-4-fluoro-2-methoxy-benzene and subsequent cleavage of the isopropylidene and the BOC group, (R)-3-[(3S,4R,5R)-4-[4-[3-(4-fluoro-2-methoxy-benzyloxy)-propoxy]-phenyl]-5-(4-methoxy-naphthalen-2-ylmethoxy)-piperidin-3-yloxy]-propane-1,2-diol as a colorless oil; MS: 650 (M+H)$^+$;

3) by alkylation with 1-(3-chloro-propoxymethyl)-4,5-difluoro-2-methoxy-benzene and subsequent cleavage of the isopropylidene and the BOC group, (R)-3-[(3S,4R,5R)-4-[4-[3-(4,5-difluoro-2-methoxy-benzyloxy)-propoxy]-phenyl]-5-(4-methoxy-naphthalen-2-ylmethoxy)-piperidin-3-yloxy]-propane-1,2-diol as a colorless oil; MS: 668 (M+H)$^+$;

4) by alkylation with 1-(3-chloro-propoxymethyl)-3,5-difluoro-2-methoxy-benzene and subsequent cleavage of the isopropylidene and the BOC group, (R)-3-[(3S,4R,5R)-4-[4-[3-(3,5-difluoro-2-methoxy-benzyloxy)-propoxy]-phenyl]-5-(4-methoxy-naphthalen-2-ylmethoxy)-piperidin-3-yloxy]-propane-1,2-diol as a colorless oil; MS: 668 (M+H)$^+$.

Example 21

(R)-1-Methoxy-3-[(3S,4R,5R)-4-[4-[3-(2-methoxy-benzyloxy)-propoxy]-phenyl]-5-(4-methoxy-naphthalen-2-ylmethoxy)-piperidin-3-ylmethoxy]-propan-2-ol In analogy to the procedure described in example 1) (h)-(l), (R)-3-[(3S,4R,5R)-4-[3-(2-methoxy-benzyloxy)-propoxy]-phenyl]-5-(4-methoxy-naphthalen-2-ylmethoxy)-piperidin-3-ylmethoxy]-propane-1,2-diol was treated with di-tert-butyl-dicarbonate in dioxane/water in the presence of sodium hydrogencarbonate to yield the (3S,4R,5R))-3-[(2R)-2,3-dihydroxy-propoxymethyl]-4-[4-[3-(2-methoxy-benzyloxy)-propoxy]-phenyl]-5-(4-methoxy-naphthalen-2-ylmethoxy)-piperidine-1-carboxylic acid tert-butyl ester. Subsequent mono-tosylation of the aforementioned diol by toluene-4-sulfochloride in pyridine led to the (3S,4R,5R)-3-[(2S)-2-hydroxy-3-(toluene-4-sulfonyloxy)-propoxymethyl]-4-[4-[3-(2-methoxy-benzyloxy)-propoxy]-phenyl]-5-(4-methoxy-naphthalen-2-ylmethoxy)-piperidine-1-carboxylic acid tert-butyl ester which after treatment with NaOH in DMSO yielded (3R,4R,5S)-4-[4-[3-(2-methoxy-benzyloxy)-propoxy]-phenyl]-3-(4-methoxy-naphthalen-2-ylmethoxy)-5-[(2R)-oxiranylmethoxymethyl]-piperidine-1-carboxylic acid tert-butyl ester. Further reaction of the epoxide with sodium methylate in a mixture of N,N-dimethylformamide and methanol gave the (3S,4R,5R)-3-[(2R)-2-hydroxy-3-methoxy-propoxymethyl]-4-{4-[3-(2-methoxy-benzyloxy)-propoxy]-phenyl}-5-(4-methoxy-naphthalen-2-ylmethoxy)-piperidine-1-carboxylic acid tert-butyl ester which was finally deprotected by treatment with hydrochloric acid in methanol to yield the (R)-1-methoxy-3-[(3S,4R,5R)-4-[4-[3-(2-methoxy-benzyloxy)-propoxy]-phenyl]-5-(4-methoxy-naphthalen-2-ylmethoxy)-piperidin-3-ylmethoxy]-propan-2-ol as a colorless foam; MS: 660 (M+H)$^+$.

Example A

Capsules

| Composition: | |
|---|---|
| 1) Compound of formula I, e.g., is (R)-1-methoxy-3-[(3S,4R,5R)-4-[4-[3-(2-methoxy-benzyloxy)-propoxy]-phenyl]-5-(4-methoxy-naphthalen-2-ylmethoxy)-piperidin-3-yloxy]-propan-2-ol | 50 mg |
| 2) Medium-chain mono-, diglyceride | 950 mg |

Production 2) is liquefied by gentle heating and 1) is dissolved in 2). The mixture is filled into hard or soft gelatine capsules of suitable size. The hard gelatine capsules may be sealed, for example using the Quali-Seal technique.

Example B

Injection Solution in Form of a Mixed Micelle Solution

| Composition | |
|---|---|
| Compound of formula I, e.g is (R)-1-methoxy-3-[(3S,4R,5R)-4-[4-[3-(2-methoxy-benzyloxy)-propoxy]-phenyl]-5-(4-methoxy-naphthalen-2-ylmethoxy)-piperidin-3-yloxy]-propan-2-ol | 3.0 mg |
| Sodium glycocholate | 98.5 mg |
| Soya lecithin | 158.2 mg |
| Sodium dihydrogen phosphate | 1.8 mg |

-continued

| Composition | |
|---|---|
| Disodium-hydrogen phosphate | 9.5 mg |
| Water for injection purposes | ad 1.0 ml |

Production

The compound of formula I, sodium glycocholate and soya lecithin are dissolved in the required amount of ethanol (or an adequate volatile solvent). The solvent is evaporated under reduced pressure and slight heating. The residue is dissolved in the buffered aqueous phase. The solution is processed by conventional procedures.

Example C

Tablets

| | Composition | |
|---|---|---|
| 1) | Compound of formula I, e.g is (R)-1-methoxy-3-[(3S,4R,5R)-4-[4-[3-(2-methoxy-benzyloxy)-propoxy]-phenyl]-5-(4-methoxy-naphthalen-2-ylmethoxy)-piperidin-3-yloxy]-propan-2-ol | 200 mg |
| 2) | Anhydrous lactose | 160 mg |
| 3) | Hydroxypropylmethylcellulose | 18 mg |
| 4) | Sodium-carboxymethylcellulose | 20 mg |
| 5) | Magnesium stearate | 2 mg |
| | Tablet weight | 400 mg |

Production 1) and 2) are mixed intensively. The mixture is thereafter moistened with an aqueous solution of 3) and kneaded, and the resulting mass is granulated, dried and sieved. The granulate is mixed with 4) and 5) and pressed to tablets of suitable size.

Upon reading the present specification various alternative embodiments will become obvious to the skilled artisan. These variations are to be considered within the scope and spirit of the subject invention, which is only to be limited by the claims that follow and their equivalents.

What is claimed is:

1. A compound of the formula:

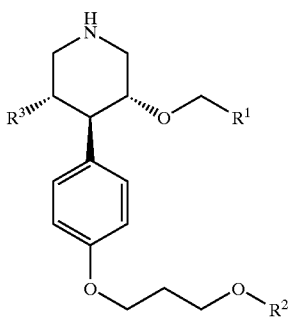

I wherein $R^1$ is naphthyl substituted by one to three $C_1$–$C_5$-alkoxy groups;

$R^2$ is phenyl; phenyl substituted by one to three substituents independently selected from the group consisting of halogen, cyano, $C_1$–$C_3$-alkoxy, and nitro; benzyl; or benzyl substituted by one to three sub substituents independently selected from the group consisting of halogen, cyano, $C_1$–$C_3$-alkoxy, and nitro;

$R^3$ is hydroxymethyl;

a pharmaceutically acceptable salt thereof.

2. The compound according to claim 1, wherein $R^1$ is naphthyl substituted by one $C_1$–$C_3$-alkoxy group.

3. The compound according to claim 2, wherein $R^1$ is naphthyl substituted by methoxy.

4. The compound according to claim 3, wherein $R^1$ is 4-methoxy-naphthalen-2-yl.

5. The compound according to claim 4, wherein $R^2$ $C_1$–$C_3$-alkoxy benzyl.

6. The compound according to claim 5, wherein $R^2$ is 2-methoxy benzyl.

7. The compound (3S,4R,5R)-[4-[4-[3-(2-methoxy-benzyloxy)-propoxy]-phenyl]-5-(4-methoxy-naphthalen-2-ylmethoxy)-piperidin-3-yl]-methanol.

8. A compound of the formula:

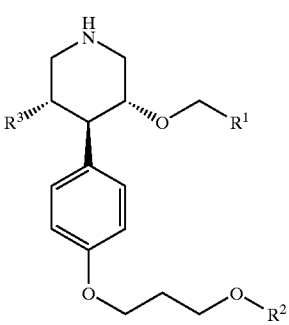

I wherein $R^1$ is naphthyl substituted by one to three $C_1$–$C_5$-alkoxy groups;

$R^2$ is phenyl; phenyl substituted by one to three substituents independently selected from the group consisting of halogen, cyano, $C_1$–$C_3$-alkoxy, and nitro; benzyl; or benzyl substituted by one to three substituents independently selected from the group consisting of halogen, cyano, $C_1$–$C_3$-alkoxy, and nitro;

$R^3$ is imidazolylmethyl;

a pharmaceutically acceptable salt thereof.

9. The compound according to claim 8, wherein $R^1$ is naphthyl substituted by one $C_1$–$C_3$-alkoxy group.

10. The compound according to claim 9, wherein $R^1$ is naphthyl substituted by methoxy.

11. The compound according to claim 10, wherein $R^1$ is 4-methoxy-naphthalen-2yl.

12. The compound according to claim 11, wherein $R^2$ is $C_1$–$C_3$-alkoxy benzyl.

13. The compound according to claim 12, wherein $R^2$ is 2-methoxy benzyl.

14. The compound (3S,4R,5R)-3-imidazol-1-ylmethyl-4-[4-[3-(2-methoxy-benzyloxy)-propoxy]-phenyl]-5-(4-methoxy-naphthalen-2-ylmethoxy)-piperidine dihydrochloride.

15. A compound of the formula:

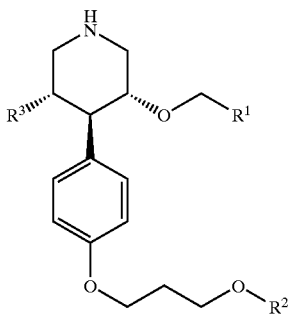

wherein
R¹ is naphthyl substituted by one to three $C_1$–$C_5$-alkoxy groups;
R² is phenyl; phenyl substituted by one to three substituents independently selected from the group consisting of halogen, cyano, $C_1$–$C_3$-alkoxy, and nitro; benzyl; or benzyl substituted by one to three substituents independently selected from the group consisting of halogen, cyano, $C_1$–$C_3$-alkoxy, and nitro;
R³ is $R^{3a}$—$(CH_2)_k$—$[CH(OR^4)]_l$—$CH_2$—O—;
$R^{3a}$ is hydrogen, hydroxy, imidazolyl, triazolyl, $C_1$–$C_3$-alkoxy, $C_1$–$C_3$-alkoxy-$C_2$–$C_3$-alkoxy, hydroxy-$C_2$–$C_3$-alkoxy, $C_1$–$C_3$-alkylamino or $C_1$–$C_3$-dialkylamino;
R⁴ is hydrogen or $C_1$–$C_3$-alkyl;
k is 1 or 2, when $R^{3a}$ is hydrogen, k is 0;
l is 1 is or 2; or
a pharmaceutically acceptable salt thereof.

16. The compound according to claim 15, wherein R¹ is naphthyl substituted by one $C_1$–$C_3$-alkoxy group.

17. The compound according to claim 16, wherein R¹ is naphthyl substituted by methoxy.

18. The compound according to claim 17, wherein R¹ is 4-methoxy-naphthalen-2yl.

19. The compound according to claim 18, wherein R² is phenyl substituted by one cyano group.

20. The compound according to claim 19, wherein R⁴ is hydrogen, is 1, K is 1, and $R^{3a}$ is methoxy-ethoxy.

21. The compound 2-[3-[4-[(3S,4R,5R)-3-[(2R)-2-hydroxy-3-(2-methoxy-ethoxy)-propoxy]-5-(4-methoxy-naphthalen-2-ylmethoxy)-piperidin-4-yl]-phenoxy]-propoxy]-benzonitrile.

22. The compound according to claim 18, wherein R² is phenyl substituted by one nitro group.

23. The compound according to claim 22, wherein R⁴ is hydrogen, is 2, K is 0, and $R^{3a}$ is hydrogen.

24. The compound (R)-3-[(3S,4R,5R)-5-(4-methoxy-naphthalen-2-ylmethoxy)-4-[4-[3-(2-nitro-phenoxy)-propoxy]-phenyl]-piperidin-3-yloxy]-propane-1,2-diol.

25. The compound according to claim 22, wherein R⁴ is hydrogen, l is 1, K is 1, and $R^{3a}$ is triazolyl.

26. The compound (R)-1-[(3S,4R,5R)-5-(4-methoxy-naphthalen-2-ylmethoxy)-4-[4-[3-(2-nitro-phenoxy)-propoxy]-phenyl]-piperidin-3-yloxy]-3-[1,2,4]triazol-1-yl-propan-2-ol.

27. The compound according to claim 22, wherein R⁴ is hydrogen, l is 1, K is 1, and $R^{3a}$ is imidazolyl.

28. The compound (R)-1-imidazol-1-yl-3-[(3S,4R,5R)-5-(4-methoxy-naphthalen-2-ylmethoxy) -4-[4-[3-(2-nitro-phenoxy)-propoxy]-phenyl]-piperidin-3-yloxy)-propan-2-ol.

29. A compound of the formula:

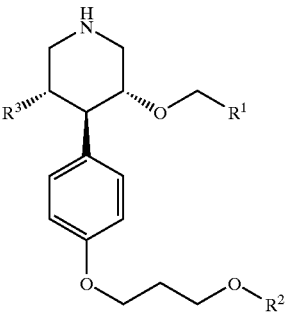

wherein
R¹ is naphthyl substituted by one to three $C_1$–$C_5$-alkoxy groups;
R² is phenyl substituted by one to three $C_1$–$C_3$-alkoxy groups or benzyl substituted by one to three $C_1$–$C_3$-alkoxy groups;
R³ is hydroxymethyl; or
a pharmaceutically acceptable salt thereof.

30. A compound of the formula:

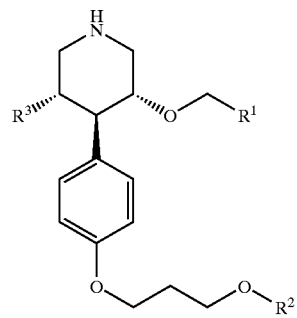

wherein
R¹ is naphthyl substituted by one to three $C_1$–$C_5$-alkoxy groups;
R² is phenyl substituted by one to three $C_1$–$C_3$-alkoxy groups or benzyl substituted by one to three $C_1$–$C_3$-alkoxy groups;
R³ is imidazolylmethyl; or
a pharmaceutically acceptable salt thereof.

* * * * *

UNITED STATES PATENT AND TRADEMARK OFFICE
CERTIFICATE OF CORRECTION

PATENT NO. : 6,673,931 B2
DATED : January 6, 2003
INVENTOR(S) : Volker Breu et al.

It is certified that error appears in the above-identified patent and that said Letters Patent is hereby corrected as shown below:

Title page,
Item [73], Assignee, reads "Hoffman-La Roche Inc., Nutley, NJ (US)" and should read
-- Hoffmann-La Roche Inc., Nutley, NJ (US) --.

Column 50,
Line 2, "one to three sub substituents" should read -- one to three substituents --.

Column 51,
Line 44, "hydrogen, is 1, K is 1," should read -- hydrogen, | is 1, K is 1, --.
Line 53, "hydrogen, is 2, K is 0," should read -- hydrogen, | is 2, K is 0, --.

Signed and Sealed this

Eleventh Day of May, 2004

JON W. DUDAS
*Acting Director of the United States Patent and Trademark Office*